(12) United States Patent
Rueger et al.

(10) Patent No.: US 10,011,644 B2
(45) Date of Patent: Jul. 3, 2018

(54) METHOD FOR PRODUCING SOLUBLE FCR AS FC-FUSION WITH INERT IMMUNOGLOBULIN FC-REGION AND USES THEREOF

(71) Applicant: Hoffmann-La Roche Inc., Little Falls, NJ (US)

(72) Inventors: Petra Rueger, Penzberg (DE); Tilman Schlothauer, Penzberg (DE); Stefan Seeber, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 437 days.

(21) Appl. No.: 14/611,645

(22) Filed: Feb. 2, 2015

(65) Prior Publication Data
US 2015/0140683 A1 May 21, 2015

Related U.S. Application Data

(63) Continuation of application No. PCT/EP2013/066065, filed on Jul. 31, 2013.

(30) Foreign Application Priority Data

Aug. 2, 2012 (EP) .................................... 12179025

(51) Int. Cl.
*C07K 14/705* (2006.01)
*G01N 33/68* (2006.01)
*C07K 14/735* (2006.01)

(52) U.S. Cl.
CPC ...... *C07K 14/705* (2013.01); *C07K 14/70535* (2013.01); *G01N 33/6854* (2013.01); *C07K 2319/30* (2013.01); *G01N 2333/70535* (2013.01)

(58) Field of Classification Search
None
See application file for complete search history.

(56) References Cited

U.S. PATENT DOCUMENTS 5,623,053 A    4/1997  Gastinel et al.

FOREIGN PATENT DOCUMENTS

| CN | 101124245 | | 2/2008 |
|---|---|---|---|
| JP | 2007-525149 | | 9/2007 |
| JP | 2008-504002 | | 2/2008 |
| JP | 2010-516769 | | 5/2010 |
| JP | 2011-526154 | | 10/2011 |
| WO | 00/40615 | | 7/2000 |
| WO | 01/03737 | A1 | 1/2001 |
| WO | 2004/062619 | | 7/2004 |
| WO | 2004/096148 | | 11/2004 |
| WO | 2005/047327 | | 5/2005 |
| WO | 2005/047327 | A2 | 5/2005 |
| WO | 2005/047327 | A8 | 5/2005 |
| WO | 2008/091682 | | 7/2008 |
| WO | 2009/158696 | | 12/2009 |
| WO | 2010/048313 | | 4/2010 |
| WO | 2011/117329 | A1 | 9/2011 |

OTHER PUBLICATIONS

Chamow SM et al. Immunoadhesions: principles and applications. 1996. Trends in Biotechnology. vol. 14. p. 52-60.*
Dumont, J.A. et al., "Monomeric Fc Fusions" Biodrugs 20:151-160 ( 2006).
Huang, C., "Receptor-Fc fusion therapeutics, traps, and MIMETIBODY™ technology" Current Opinion in Biotechnology 20:692-699 ( 2009).
Lo et al., "High level expression and secretion of Fc-X fusion proteins in mammalian cells" Protein Engineering 11(6):495-500 (1998).
Ying, T. et al., "Soluble Monomeric IgG1 Fc" The Journal of Biological Chemistry 287(23):19399-19408 (Jun. 1, 2012).

* cited by examiner

*Primary Examiner* — Paul J Holland
(74) *Attorney, Agent, or Firm* — Grant Kalinowski

(57) ABSTRACT

Herein is a fusion polypeptide with the formula R1-FC-R2, wherein R1 denotes a first Fc-receptor, R2 denotes a second Fc-receptor, and FC denotes a heavy chain Fc-region polypeptide, wherein R1 or R2 or both are present, wherein FC does not substantially bind to R1 and/or R2 and uses thereof.

3 Claims, 10 Drawing Sheets

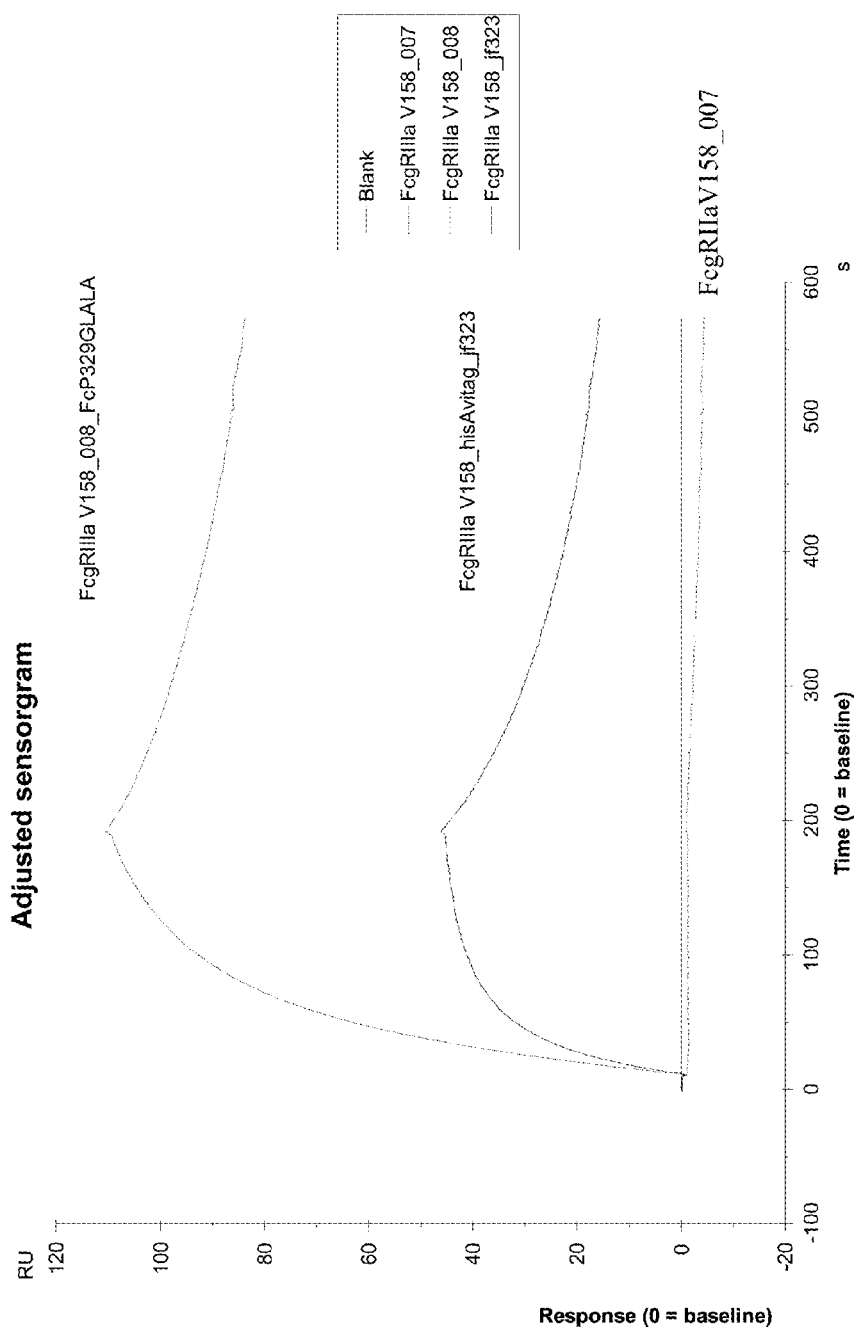

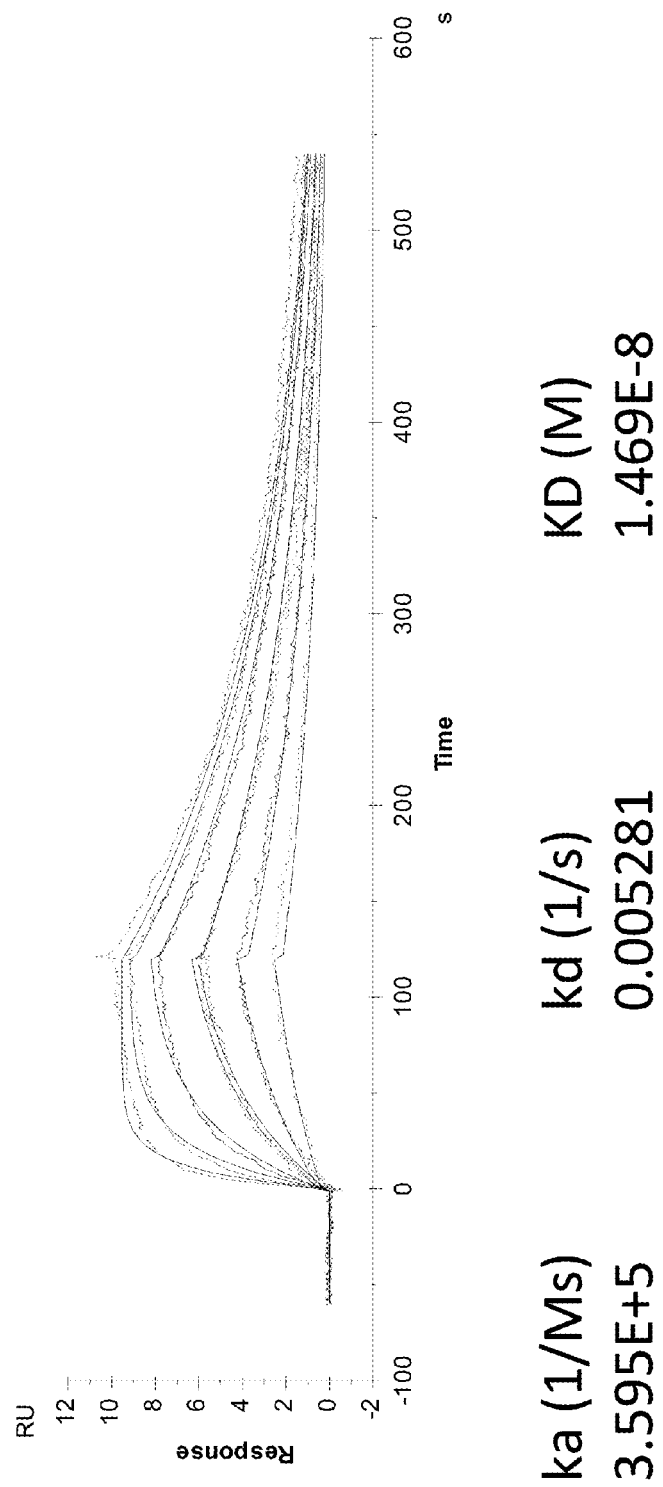

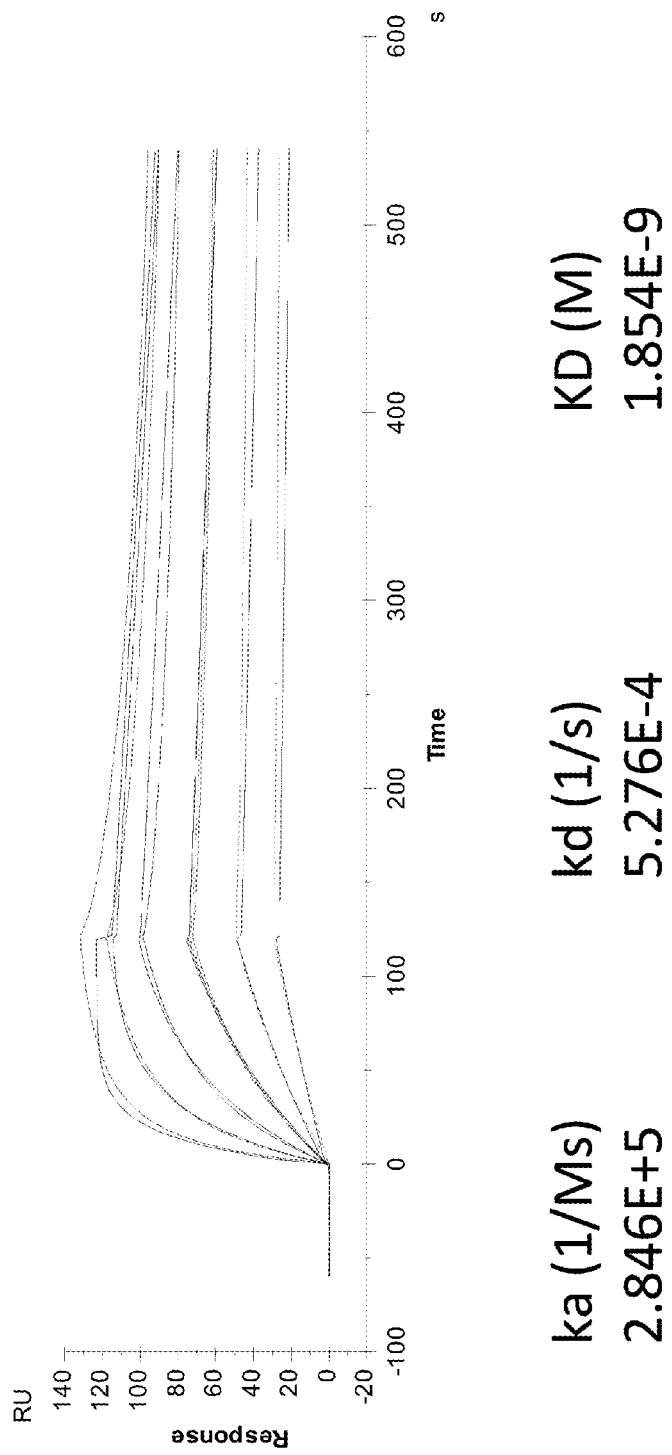

METHOD FOR PRODUCING SOLUBLE FCR AS FC-FUSION WITH INERT IMMUNOGLOBULIN FC-REGION AND USES THEREOF

RELATED APPLICATIONS

This application is a continuation of International Application No. PCT/EP2013/066065, filed Jul. 31, 2013, which claims priority to European application number EP12179025, filed Aug. 2, 2012, the contents of which are incorporated herein by reference.

SEQUENCE LISTING

The instant application contains a Sequence Listing which has been submitted in ASCII format via EFS-Web and is hereby incorporated by reference in its entirety. Said ASCII copy, created on Jan. 27, 2015, is named P31131US_SEQUENCE_LISTING.txt and is 67,407 bytes in size.

FIELD OF THE INVENTION

Herein is reported a method for the production of soluble Fc-receptors as fusion polypeptide with an inert immunoglobulin Fc-region preventing self-aggregation and uses thereof, such as FcR chromatography columns, determination of FcR interaction of low affinity antibodies.

BACKGROUND OF THE INVENTION

An immunoglobulin contains in general two light polypeptide chains and two heavy polypeptide chains. Each of the heavy and light polypeptide chains comprises a variable region (generally the amino terminal portion of the polypeptide chain) which contains a binding domain that is able to interact with an antigen. Each of the heavy and light polypeptide chains also comprises a constant region (generally the carboxyl terminal portion). The constant region of the heavy chain mediates the binding of the immunoglobulin e.g. to cells bearing an Fc gamma receptor (FcγR), such as phagocytic cells, or to cells bearing the neonatal Fc-receptor (FcRn) also known as Brambell receptor, and also mediates the binding to some factors including factors of the classical complement system such as component (C1q).

Hulett and Hogarth (Hulett, M. D. and Hogarth, P. M., Adv. Immunol. 57 (1994) 1-127) reported that the extracellular receptors for the Fc part of immunoglobulins of class G are a family of transmembrane glycoproteins comprising three different receptor types having different binding specificity: FcγRI, FcγRII, and FcγRIII. Receptors of type I interact with non-complexed IgG, whereas receptors of type II and III interact preferably with complexed IgG.

Human FcγRIII (CD 16) exists in two isoforms and two polymorphic forms. The first isoform FcγRIIIa is a transmembrane molecule encoded by a different gene than the second isoform FcγRIIIb, which is a GPI-anchored membrane protein. Polymorphic form V159 has a valine residue at position 159 of the amino acid sequences whereas the polymorphic form F159 has a phenylalanine residue at position 159.

For the IgG class of immunoglobulins, ADCC and ADCP are governed by engagement of the Fc-region with a family of receptors referred to as Fc-gamma (Fcγ) receptors (FcγRs). In humans, this protein family comprises FcγRI (CD64), FcγRII (CD32), including isoforms FcγRIIA, FcγRIIB, and FcγRIIC, and FcγRIII (CD16), including isoforms FcγRIIIA and FcγRIIIB (Raghavan and Bjorkman, Annu Rev. Cell Dev. Biol. 12 (1996) 181-220; Abes, et al., Expert Reviews (2009) 735-747). FcγRs are expressed on a variety of immune cells, and formation of the Fc/FcγR complex recruits these cells to sites of bound antigen, typically resulting in signaling and subsequent immune responses such as release of inflammation mediators, B-cell activation, endocytosis, phagocytosis, and cytotoxic attack. Furthermore, whereas FcγRI, FcγRIIA/C, and FcγRIIIA are activating receptors characterized by an intracellular immunoreceptor tyrosine-based activation motif (ITAM), FcγRIIB has an inhibitory motif (ITIM) and is therefore inhibitory. While FcγRI binds monomeric IgG with high affinity, FcγRIII and FcγRII are low-affinity receptors, interacting with complexed or aggregated IgG.

The binding of IgG to activating and inhibitory Fcγ receptors or the first component of complement (C1q) depends on residues located in the hinge region and the CH2 domain. Two regions of the CH2 domain are critical for FcγRs and complement C1q binding, and have unique sequences. Substitution of human IgG1 and IgG2 residues at positions 233-236 and IgG4 residues at positions 327,330 and 331 greatly reduced ADCC and CDC (Armour, et al., Eur. J. Immunol. 29 (1999) 2613-2624; Shields, et al., J. Biol. Chem. 276 (2001) 6591-6604). Idusogie, et al. (J. Immunol 166 (2000) 2571-2575) mapped the C1q binding site for the therapeutic antibody Rituxan® and showed that the Pro329Ala substitution reduced the ability of Rituximab to bind C1q and activate complement. Substitution of Pro329 with Ala has been reported to lead to a reduced binding to the FcγRI, FcγRII and FcγRIIIA receptors (Shields, et al., J. Biol. Chem. 276 (2001) 6591-6604) but this mutation has also been described as exhibiting a wild-type-like binding to the FcγRI and FcγRII and only a very small decrease in binding to the FcγRIIIA receptor (Table 1 and Table 2 in EP 1 068 241, Genentech).

In WO 2010/048313 recombinant FcRn and variants thereof for purification of Fc-containing fusion proteins are reported. The high level expression and secretion of Fc-X fusion proteins in mammalian cells is reported by Lo et al. (Lo, K.-M., et al., Prot. Eng. 11 (1998) 495-500). Dumont, F. A., et al. (Biodrugs 20 (2006) 151-160) report monomeric Fc-fusions. Receptor-Fc fusion therapeutics, traps, and MIMETIBODY™ technology is reported by Huang, C. (Curr. Opin. Biotechnol. 20 (2009) 592-599). In WO 01/03737 immunoglobulin fusion proteins are reported. The expression and export of anti-obesity proteins as Fc fusion proteins is reported in WO 00/40615.

SUMMARY OF THE INVENTION

It has been found that soluble Fc-receptors can be produced by expressing the Fc-receptor as fusion polypeptide with an Fc-region that does not substantially bind to the fused Fc-receptor. Using a fusion polypeptide for the expression of the Fc-receptor increases the obtainable yield of the Fc-receptor either in form of the fusion polypeptide or as isolated receptor. Additionally the fusion polypeptide as reported herein provides for an increased flexibility for combining more than one copy of an Fc-receptor in a single molecule, e.g. for increased avidity, or for combining different Fc-receptors (of different origin or of different type or both) in a single molecule.

One aspect as reported herein is a fusion polypeptide according to formula I

R1-FC-R2    (formula I)

wherein
R1 denotes a first Fc-receptor,
R2 denotes a second Fc-receptor, and
FC denotes a heavy chain Fc-region polypeptide,
wherein R1 or R2 or both are present,
wherein FC does not substantially bind to R1 and/or R2.
In one embodiment the fusion polypeptide has the formula II R1-CS1-L1-CS2-FC-CS3-L2-CS4-R2 (formula II)

wherein
R1 denotes a first Fc-receptor,
R2 denotes a second Fc-receptor,
FC denotes a heavy chain Fc-region polypeptide,
CS1 denotes a first cleavage site,
CS2 denotes a second cleavage site,
CS3 denotes a third cleavage site,
CS4 denotes a fourth cleavage site,
L1 denotes a first intervening amino acid sequence, and
L2 denotes a second intervening amino acid sequence,
wherein R1 or R2 or both are present,
wherein any one of CS1, CS2, CS3, CS4 can independently of each other be present or absent,
wherein L1 and L2 can independently of each other be present or absent,
wherein FC does not substantially bind to R1 and/or R2.

In one embodiment R1 and R2 are independently of each other selected from the group of human Fcgamma-receptor, human neonatal Fc-receptor, murine Fc-receptor, and rabbit neonatal Fc-receptor.

In one embodiment the human Fcgamma-receptor is selected from human FcγRI (CD64), human FcγRII (CD32), human FcγRIIA, human FcγRIIB, human FcγRIIC, human FcγRIII (CD16), human FcγRIIIA, and human FcγRIIIB In one embodiment the human neonatal Fc-receptor is human FcRn.

In one embodiment the murine Fc-receptor is selected from murine FcγRI (CD64), murine FcγRII (CD32), murine FcγRIIB, murine FcγRIII (CD16), murine FcγRIII-2 (CD16-2), and murine FcγRIV.

In one embodiment the FC is a variant of a heavy chain polypeptide selected from the group of human IgG heavy chain polypeptide, murine IgG heavy chain polypeptide, rabbit IgG heavy chain polypeptide.

In one embodiment the FC is a variant of a heavy chain polypeptide selected from the group of human IgG1 heavy chain polypeptide, human IgG2 heavy chain polypeptide, human IgG3 heavy chain polypeptide, human IgG4 heavy chain polypeptide, murine IgG1 heavy chain polypeptide, murine IgG2 heavy chain polypeptide, murine IgG2a heavy chain polypeptide, murine IgG3 heavy chain polypeptide, rabbit IgG heavy chain polypeptide.

In one embodiment the heavy chain Fc-region polypeptide has an amino acid mutation at one or more of position 234, 235, 236, 237, 238, 239, 253, 254, 265, 266, 267, 268, 269, 270, 288, 297, 298, 299, 307, 311, 327, 328, 329, 330, 331, 332, 434, and 435.

In one embodiment one or more of the Fc-receptors is an Fc gamma receptor.

In one embodiment the human IgG1 heavy chain polypeptide has a mutation at one or more of amino acid positions 233, 234, 235, 236, 265, 297, 329, and 331.

In one embodiment the human IgG1 heavy chain polypeptide has one or more of the amino acid mutations E233P, L234A, L235A, L235E, AG236, D265A, N297A, N297D, P329A, P329G, and P331S.

In one embodiment the human IgG1 heavy chain polypeptide has the amino acid mutations L234A and L235A and one or more of E233P, L235E, AG236, D265A, N297A, N297D, P329A, P329G, and P331S.

In one embodiment the human IgG1 heavy chain polypeptide has the amino acid mutations L234A and L235A and P329A or P329G.

In one embodiment the human IgG2 heavy chain polypeptide has mutations at one or more of amino acid positions 233, 234, 235, 236, 265, and 329.

In one embodiment the human IgG4 heavy chain polypeptide has a mutation at one or more of amino acid positions 228, 235, 265, and 329.

In one embodiment the human IgG4 heavy chain polypeptide has one or more of the mutations S228P, L235E, P329A, and P329G.

In one embodiment the human IgG4 heavy chain polypeptide has the mutations S228P and L235E and P329A or P329G.

In one embodiment the heavy chain Fc-region polypeptide has an amino acid mutation at one or more of position 248, 250, 251, 252, 253, 254, 255, 256, 257, 272, 285, 288, 290, 291, 308, 309, 310, 311, 314, 385, 386, 387, 428, 433, 434, 435, and 436.

In one embodiment one or more of the Fc-receptors is an FcRn.

In one embodiment the human IgG heavy chain polypeptide has a mutation at one or more of the amino acid positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439, and/or 447.

In one embodiment the human IgG heavy chain polypeptide that has a reduced binding to FcRn has one or more amino acid alterations at the amino acid positions 252, 253, 254, 255, 288, 309, 386, 388, 400, 415, 433, 435, 436, 439, and/or 447.

In one embodiment the human IgG heavy chain polypeptide that has a reduced binding to FcRn has the amino acid mutations I253A, H310A, and H435A.

In one embodiment the intervening amino acid sequence is selected from a first group comprising (G3S)3, (G3S)4, (G3S)5, (G3S)6, (G4S)3, (G4S)4, (G4S)5, (G5S)2, (G5S)3, and (G5S)4, or from a second group comprising Arg-tag, Avi-tag, His-Avi-tag, His-tag, Flag-tag, 3xFlag-tag, Strep-tag, Nano-tag, SBP-tag, c-myc-tag, S-tag, calmodulin-binding-peptide, cellulose-binding-domain, chitin-binding-domain, GST-tag, or MBP-tag, or from combinations of two elements of these group.

In one embodiment the cleavage site is selected from IgA-protease protease cleavage site, Granzyme B protease cleavage site, Tev protease cleavage site, Precision protease cleavage site, Thrombin cleavage site, Faktor10a protease site, IdeS protease cleavage site, Enterokinase cleavage site, or a SUMO protease cleavage site.

In one embodiment the fusion polypeptide does not comprise an additional protease cleavage site but an inherent protease cleavage site, such as e.g. a papain cleavage site, a pepsin cleavage site, or an IdeS protease cleavage site.

One aspect as reported herein is a dimeric fusion polypeptide comprising two fusion polypeptides as reported herein.

In one embodiment the first FC comprises the mutation T366W and optionally the mutation S354C and the second FC comprises the mutations T366S, L368A and Y407V and optionally the mutation Y349C.

In one embodiment the fusion polypeptide is characterized in that
a) R1 and R2 of the first and second polypeptide are identical,
b) R1 and R2 of the first fusion polypeptide are identical, R1 and R2 of the second fusion polypeptide are identical but different from R1 and R2 of the first fusion polypeptide,
c) R1 of the first and second fusion polypeptide are identical and R2 of the first and second polypeptide are identical but different from R1,
d) R1 of the first and second fusion polypeptide are identical and both R2 are absent,
e) R1 of the first and second fusion polypeptide are different and both R2 are absent,
f) R2 of the first and second fusion polypeptide are identical and both R1 are absent,
g) R2 of the first and second fusion polypeptide are different and both R1 are absent,
h) R1 of the first fusion polypeptide and R2 of the second polypeptide are different and R2 of the first fusion polypeptide is absent and R1 of the second polypeptide is absent.

One aspect as reported herein is a method for the production of a soluble Fc-receptor comprising the following steps
a) cultivating a cell comprising a nucleic acid encoding a fusion polypeptide as reported herein,
b) recovering the fusion polypeptide from the cell or the cultivation medium,
c) optionally cleaving the fusion polypeptide with a protease, thereby producing a soluble Fc-receptor.

One aspect as reported herein is the use of an immobilized fusion polyp eptide or an immobilized dimeric fusion polypeptide as reported herein as affinity chromatography ligand.

One aspect as reported herein is the use of an immobilized fusion polypeptide or an immobilized dimeric fusion polypeptide as reported herein for determining the Fc-receptor binding of an antibody.

In one embodiment the fusion polypeptide is bound to a solid phase.

One aspect as reported herein is a pharmaceutical composition comprising a fusion polypeptide as reported herein.

One aspect as reported herein is the use of a fusion polypeptide as reported herein in the manufacture of a medicament.

In one embodiment the medicament is for the treatment of an inflammatory disease.

In one embodiment the disease is a disease characterized by increased antibody levels.

In one embodiment the disease is an autoimmune disease.
In one embodiment the disease is rheumatoid arthritis.

DETAILED DESCRIPTION OF THE INVENTION

Description of the Figures

FIG. 3 12% Bis Tris Gel+/−DTT; Cleavage of FcgammaRIIIaV158-Avi-Fc LALA P239G with PreScission® protease (lane 3, 8) respectively IgA protease (lane 2, 7): unspecific cleavage with PP can be seen (lane 3, 8).

FIG. 6 BIAcore sensorgram of the response of the FcgammaRIIIaV158-Fc LALA P329G fusion polypeptide display more than 100 Response units in comparison to the FcgammaRIIIaV158 with 40 RU; FcgRIIIa V 158_008 denotes the non-cleaved fusion polypeptide, FcgRIIIa V 158_007 denotes a shortened non-functional variant of the FcgRIIIa (=control), FcgRIIIa V 158_jf323 denotes the intact HisAvi-tag comprising functional variant of FcgRIIIa.
FIG. 7C Sensogram of cleaved Fcgamma receptor V158-Fc LALA P329G fusion polypeptide.
FIG. 7D Sensogram of non-functional Fcgamma receptor V158-Fc LALA P329G fusion polypeptide (=control).

DEFINITIONS

Figure 1:
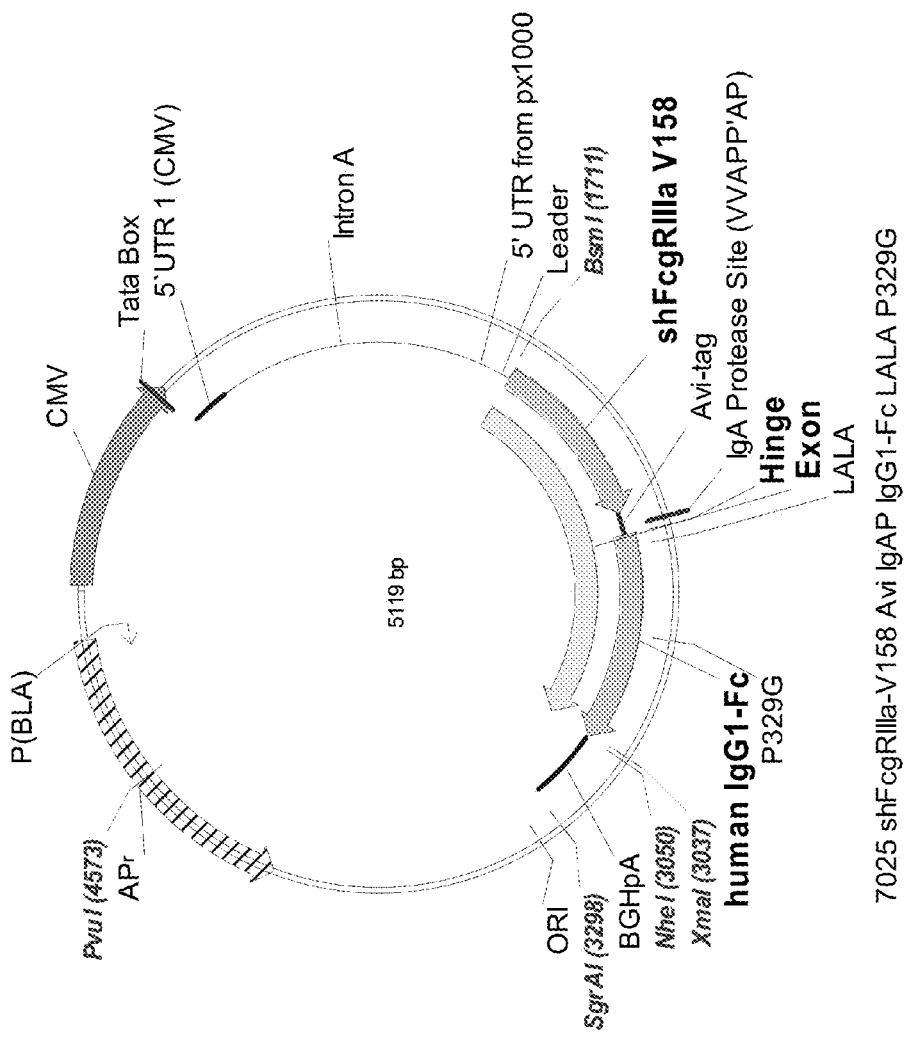
FIG. 1 Plasmid map of fusion polypeptide expression plasmid.

The term "binding to an Fc-receptor" denotes the binding of an Fc-region to an Fc-receptor in, for example, a BIAcore® assay (Pharmacia Biosensor AB, Uppsala, Sweden).

In the BIAcore® assay the Fc-receptor is bound to a surface and binding of the analyte, e.g. an Fc-region comprising fusion polypeptide or an antibody, is measured by surface plasmon resonance (SPR). The affinity of the binding is defined by the terms ka (association constant: rate constant for the association of the Fc-region fusion polypeptide or conjugate to form an Fc-region/Fc-receptor complex), kd (dissociation constant; rate constant for the dissociation of the Fc-region fusion polypeptide or conjugate from an Fc-region/Fc-receptor complex), and KD (kd/ka). Alternatively, the binding signal of a SPR sensorgram can be compared directly to the response signal of a reference, with respect to the resonance signal height and the dissociation behaviors.

The term "CH2 domain" denotes the part of an antibody heavy chain polypeptide that extends approximately from EU position 231 to EU position 340 (EU numbering system according to Kabat). In one embodiment a CH2 domain has the amino acid sequence of SEQ ID NO: 01 (APELLGGPSVFLFPPKPKDTLMISRTPEVTCVWDVSHEDPEVKFNWYVDGVEVHNAKTKPREEQESTYRWSVLTVLHQDWLNGKEYKCKVSNKALPAPIEKTISKAK). The CH2 domain is unique in that it is not closely paired with another domain. Rather, two N-linked branched carbohydrate chains are interposed between the two CH2 domains of an intact native Fc-region. It has been speculated that the carbohydrate may provide a substitute for the domain-domain pairing and help stabilize the CH2 domain. Burton, Mol. Immunol. 22 (1985) 161-206.

The term "CH3 domain" denotes the part of an antibody heavy chain polypeptide that extends approximately from EU position 341 to EU position 446. In one embodiment the CH3 domain has the amino acid sequence of SEQ ID NO: 02 (GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG).

The term "class" of an antibody denotes the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "Fc-region" denotes the C-terminal region of an immunoglobulin. The Fc-region is a dimeric molecule comprising two disulfide-linked antibody heavy chain Fc-region polypeptides (Fc-region polypeptide chains). An Fc-region can be generated by papain digestion, or IdeS digestion, or trypsin digestion of an intact (full length) antibody or can be produced recombinantly.

The Fc-region obtainable from a full length antibody or immunoglobulin comprises residues 226 (Cys) to the C-terminus of the full length heavy chain and, thus, comprises a part of the hinge region and two or three constant domains, i.e. a CH2 domain, a CH3 domain, and optionally a CH4 domain. It is known from U.S. Pat. Nos. 5,648,260 and 5,624,821 that the modification of defined amino acid residues in the Fc-region results in phenotypic effects.

The formation of the dimeric Fc-region comprising two identical or non-identical antibody heavy chain fragments is mediated by the non-covalent dimerization of the comprised CH3 domains (for involved amino acid residues see e.g. Dall'Acqua, Biochem. 37 (1998) 9266-9273). The Fc-region is covalently stabilized by the formation of disulfide bonds in the hinge region (see e.g. Huber, et al., Nature 264 (1976) 415-420; Thies, et al., J. Mol. Biol. 293 (1999) 67-79). The introduction of amino acid residue changes within the CH3 domain in order to disrupt the dimerization of CH3-CH3 domain interactions do not adversely affect the FcRn binding due to the location of the CH3-CH3-domain dimerization involved residues are located on the inner interface of the CH3 domain, whereas the residues involved in Fc-region-FcRn interaction are located on the outside of the CH2-CH3 domain.

The Fc-region associated effector functions are initiated by the interaction of the Fc-region with effector function specific cell surface receptors. Mostly antibodies of the IgG1 isotype can effect receptor activation, whereas antibodies of the IgG2 and IgG4 isotype do not have effector function or have limited effector function.

The effector function eliciting receptors are the Fc-receptor types (and sub-types) FcγRI, FcγRII and FcγRIII. The effector functions associated with an IgG1 isotype can be reduced by introducing specific amino acid changes in the lower hinge region, such as L234A and/or L235A, which are involved in FcγR and C1q binding. Also certain amino acid residues, especially located in the CH2 and/or CH3 domain, are associated with the circulating half-life of an antibody molecule or an Fc-region fusion polypeptide in the blood stream. The circulatory half-life is determined by the binding of the Fc-region to the neonatal Fc-receptor (FcRn).

The numbering of the amino acid residues in the constant region of an antibody is made according to the EU index of Kabat (Kabat et al. 1991, Sequences of Proteins of immunological Interest, U.S. Department of Public Health, Bethesda, Md.).

The term "Fc-region of human origin" denotes the C-terminal region of an immunoglobulin heavy chain of human origin that contains at least a part of the hinge region, the CH2 domain and the CH3 domain. In one embodiment, a human IgG heavy chain Fc-region extends from Cys226, or from Pro230, to the carboxyl-terminus of the heavy chain. However, the C-terminal lysine (Lys447) of the Fc-region may or may not be present. Unless otherwise specified herein, numbering of amino acid residues in the Fc-region or constant region is according to the EU numbering system, also called the EU index, as described in Kabat, E. A., et al., Sequences of Proteins of Immunological Interest, 5th ed., Public Health Service, National Institutes of Health, Bethesda, Md. (1991), NIH Publication 91-3242.

The term "FcRn binding portion of an Fc-region" denotes the part of an antibody heavy chain polypeptide that extends approximately from EU position 243 to EU position 261 and approximately from EU position 275 to EU position 293 and approximately from EU position 302 to EU position 319 and approximately from EU position 336 to EU position 348 and approximately from EU position 367 to EU position 393 and EU position 408 and approximately from EU position 424 to EU position 440. In one embodiment one or more of the following amino acid residues according to the EU numbering of Kabat are altered F243, P244, P245 P, K246, P247, K248, D249, T250, L251, M252, I253, S254, 8255, T256, P257, E258, V259, T260, C261, F275, N276, W277, Y278, V279, D280, V282, E283, V284, H285, N286, A287, K288, T289, K290, P291, R292, E293, V302, V303, S304, V305, L306, T307, V308, L309, H310, Q311, D312, W313, L314, N315, G316, K317, E318, Y319, I336, S337, K338, A339, K340, G341, Q342, P343, R344, E345, P346, Q347, V348, C367, V369, F372, Y373, P374, S375, D376, I377, A378, V379, E380, W381, E382, S383, N384, G385, Q386, P387, E388, N389, Y391, T393, S408, S424, C425, S426, V427, M428, H429, E430, A431, L432, H433, N434, H435, Y436, T437, Q438, K439, and S440 (EU numbering).

A polypeptide chain of a wild-type human Fc-region of the IgG1 isotype has the following amino acid sequence:

```
                                            (SEQ ID NO: 03)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.
```

A polypeptide chain of a variant human Fc-region of the IgG1 isotype with the mutations L234A, L235A has the following amino acid sequence:

```
                                            (SEQ ID NO: 04)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.
```

A polypeptide chain of a variant human Fc-region of the IgG1 isotype with T366S, L368A and Y407V mutations has the following amino acid sequence:

```
                                            (SEQ ID NO: 05)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK.
```

A polypeptide chain of a variant human Fc-region of the IgG1 isotype with a T366W mutation has the following amino acid sequence:

```
                                            (SEQ ID NO: 06)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK.
```

A polypeptide chain of a variant human Fc-region of the IgG1 isotype with a L234A, L235A and T366S, L368A and Y407V mutations has the following amino acid sequence:

```
                                            (SEQ ID NO: 07)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK.
```

A polypeptide chain of a variant human Fc-region of the IgG1 isotype with a L234A, L235A and T366W mutation has the following amino acid sequence:

```
                                            (SEQ ID NO: 08)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK.
```

A polypeptide chain of a variant human Fc-region of the IgG1 isotype with a P329G mutation has the following amino acid sequence:

```
                                            (SEQ ID NO: 09)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.
```

A polypeptide chain of a variant human Fc-region of the IgG1 isotype with a L234A, L235A and P329G mutation has the following amino acid sequence:

```
                                            (SEQ ID NO: 10)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK.
```

A polypeptide chain of a variant human Fc-region of the IgG1 isotype with a P239G and T366S, L368A and Y407V mutation has the following amino acid sequence:

```
                                            (SEQ ID NO: 11)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK.
```

A polypeptide chain of a variant human Fc-region of the IgG1 isotype with a P329G and T366W mutation has the following amino acid sequence:

```
                                            (SEQ ID NO: 12)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK.
```

A polypeptide chain of a variant human Fc-region of the IgG1 isotype with a L234A, L235A, P329G and T366S, L368A and Y407V mutation has the following amino acid sequence:

```
                                            (SEQ ID NO: 13)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVCTLPPSRDELTKNQVSLSCAVK

GFYPSDIAVEWESNGQPENNYKTTPPVLDSDGSFFLVSKLTVDKSRWQQG

NVFSCSVMHEALHNHYTQKSLSLSPGK.
```

A polypeptide chain of a variant human Fc-region of the IgG1 isotype with a L234A, L235A, P329G and T366W mutation has the following amino acid sequence:

```
                                            (SEQ ID NO: 14)
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALGAPIEKTISKAKGQPREPQVYTLPPCRDELTKNQVSLWCLVK

GFYPSDIAVEWESNGQPENNYKTTPPVLDSDGSFFLYSKLTVDKSRWQQG

NVFSCSVMHEALHNHYTQKSLSLSPGK.
```

A polypeptide chain of a wild-type human Fc-region of the IgG4 isotype has the following amino acid sequence:

```
                                            (SEQ ID NO: 15)
ESKYGPPCPSCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK.
```

A polypeptide chain of a variant human Fc-region of the IgG4 isotype with a S228P and L235E mutation has the following amino acid sequence:

(SEQ ID NO: 16)
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK.

A polypeptide chain of a variant human Fc-region of the IgG4 isotype with a S228P, L235E and P329G mutation has the following amino acid sequence:

(SEQ ID NO: 17)
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLGSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK.

The term "Fe-receptor", short "FcR", denotes a receptor that binds to an Fc-region. In one embodiment the FcR is a native sequence human FcR. Moreover, in one embodiment the FcR is an FcR which binds an IgG antibody (an Fc gamma receptor) and includes receptors of the FcγRI, FcγRII, and FcγRIII subclasses, including allelic variants and alternatively spliced forms thereof. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, Annu Rev. Immunol 9 (1991) 457-492, Capel, et al., Immunomethods 4 (1994) 25-34, de Haas, et al., J. Lab. Clin. Med. 126 (1995) 330-341. Other FcRs are encompassed by the term "FcR" herein. The term also includes the neonatal receptor, FcRn, which is responsible for the transfer of maternal IgGs to the fetus (see e.g. Guyer, et al., J. Immunol. 117 (1976) 587; Kim, et al., J. Immunol. 24 (1994) 249).

The term "Fe gamma receptor", short "FcγR" or "FegammaR", denote any member of the family of proteins that bind the IgG antibody Fc-region and are encoded by an FcγR gene. In humans this family includes but is not limited to FcγRI (CD64), including isoforms FcγRIA, FcγRIB, and FcγRIC, FcγRII (CD32), including isoforms FcγRIIA (including allotypes H131 and R131), FcγRIIB (including FcγRIIB-1 and FcγRIIB-2), and FcγRIIc, and FcγRIII (CD16), including isoforms FcγRIIIA (including allotypes V158 and F158; Swiss-Prot entry P08637; N-terminus-MRTEDLPKAVVFLEPQWYRVLEKDSVTLKCQGAY-SPEDNSTQWFHNESLISSQASSYFIDAATVDDSGEY-RCQTNLSTLSDPVQLEVHIGWLLLQAPRWVFKEED-PIHLRCHSWKNTALHKVTYLQNGKGRKYFHHNSD FYIPKATLKDSGSYFCRGLVGSKNVSSET-VNITITQGLAVSTISSFFPPGYQ-C-terminus; SEQ ID NO: 18) and FcγRIIIb (including allotypes FcγRIIB-NA1 and FcγRIIB-NA2) (see e.g. Jefferis et al., Immunol. Lett. 82 (2002) 57-65, entirely incorporated by reference), as well as FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD16), and FcγRIII-2 (CD16-2), as well as or FcγR isoforms or allotypes. The Fc-region-FcγR interaction involved amino acid residues are 234-239 (lower hinge region), 265-269 (B/C loop), 297-299 (D/E loop), and 327-332 (F/G) loop (Sondermann, et al., Nature 406 (2000) 267-273). Amino acid mutations that result in a decreased binding/affinity for the FcγRI, FcγRIIA, FcγRIIB, and/or FcγRIIIA include N297A (concomitantly with a decreased immunogenicity and prolonged half-life binding/affinity) (Routledge, et al., Transplantation 60 (1995) 847; Friend et al., Transplantation 68 (1999) 1632; Shields et al., J. Biol. Chem. 276 (1995) 6591), residues 233-236 (Ward and Ghetie, Ther. Immunol. 2 (1995) 77; Armour et al., Eur. J. Immunol. 29 (1999) 2613). Some exemplary amino acid substitutions are described in U.S. Pat. Nos. 7,355,008 and 7,381,408.

The term "neonatal Fc-receptor", short "FcRn", denote a protein that binds the IgG antibody Fc-region and is encoded at least in part by an FcRn gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin. The interacting amino acid residues of the Fc-region with the FcRn are near the junction of the CH2 and CH3 domains. The Fc-region-FcRn contact residues are all within a single IgG heavy chain. The involved amino acid residues are 248, 250-257, 272, 285, 288, 290-291, 308-311, and 314 (all in the CH2 domain) and amino acid residues 385-387, 428, and 433-436 (all in the CH3 domain). Amino acid mutations that result in an increased binding/affinity for the FcRn include T256A, T307A, E380A, and N434A (Shields et al., J. Biol. Chem. 276 (2001) 6591).

The amino acid residues of the neonatal Fc receptor that are conserved across species are the histidine residues at position 310 and 435 in the Fc-region. These residues are responsible for the pH dependence of the Fc-region FcRn interaction (see, e.g., Victor, G., et al., Nature Biotechnol. 15 (1997) 637-640); Dall'Acqua, W. F., et al. J. Immunol. 169 (2002) 5171-5180). Fc-region mutations that attenuate interaction with FcRn can reduce antibody half-life.

The term "hinge region" denotes the part of an antibody heavy chain polypeptide that joins the CH1 domain and the CH2 domain, e.g. from about position 216 to position about 230 according to the EU number system of Kabat. The hinge region is normally a dimeric molecule consisting of two polypeptides with identical amino acid sequence. The hinge region generally comprises about 25 amino acid residues and is flexible allowing the antigen binding regions to move independently. The hinge region can be subdivided into three domains: the upper, the middle, and the lower hinge domain (Roux, et al., J. Immunol. 161 (1998) 4083).

The term "lower hinge region" of an Fc-region denotes the stretch of amino acid residues immediately C-terminal to the hinge region, i.e. residues 233 to 239 of the Fc-region according to the EU numbering of Kabat.

The term "wild-type Fc-region" denotes an amino acid sequence identical to the amino acid sequence of an Fc-region found in nature. Wild-type human Fc-regions include a native human IgG1 Fc-region (non-A and A allotypes), native human IgG2 Fc-region, native human IgG3 Fc-region, and native human IgG4 Fc-region as well as naturally occurring variants thereof.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

The term "polypeptide" denotes a polymer consisting of amino acids joined by peptide bonds, whether produced naturally or synthetically. Polypeptides of less than about 20 amino acid residues may be referred to as "peptides", whereas molecules consisting of two or more polypeptides or comprising one polypeptide of more than 100 amino acid residues may be referred to as "proteins". A polypeptide may also comprise non-amino acid components, such as carbohydrate groups, metal ions, or carboxylic acid esters. The non-amino acid components may be added by the cell, in which the polypeptide is expressed, and may vary with the type of cell. Polypeptides are defined herein in terms of their amino acid backbone structure or the nucleic acid encoding the same. Additions such as carbohydrate groups are generally not specified, but may be present nonetheless.

The term "amino acid sequence tag" denotes a sequence of amino acid residues connected to each other via peptide bonds that has specific binding properties. In one embodiment the amino acid sequence tag is an affinity or purification tag. In one embodiment the amino acid sequence tag is selected from the group comprising Arg-tag, His-tag, Avi-tag, His-Avi-tag, Flag-tag, 3xFlag-tag, Strep-tag, Nano-tag, SBP-tag, c-myc-tag, S-tag, calmodulin-binding-peptide, cellulose-binding-domain, chitin-binding-domain, GST-tag, and MBP-tag. In one embodiment the amino acid sequence tag is selected from the group comprising SEQ ID NO: 19 (RRRRR), SEQ ID NO: 20 (RRRRRR), SEQ ID NO: 21 (Avi-tag), SEQ ID NO: 22 (His-Avi-tag), SEQ ID NO: 23 (HHHHHH), SEQ ID NO: 24 (KDHLIHNVHKEFHAHAHNK), SEQ ID NO: 25 (DYKDDDDK), SEQ ID NO: 26 (DYKDHDGDYKDHDIDYKDDDDK), SEQ ID NO: 27 (AWRHPQFGG), SEQ ID NO: 28 (WSHPQFEK), SEQ ID NO: 29 (MDVEAWLGAR), SEQ ID NO: 30 (MDVEAWLGARVPLVET), SEQ ID NO: 31 (MDEKTTGWRGGHVVEGLAGELEQLRARLEHHPQGQREP), SEQ ID NO: 32 (EQKLISEEDL), SEQ ID NO: 33 (KETAAAKFERQHMDS), SEQ ID NO: 34 (KRRWKKNFIAVSAANRFKKISSSGAL), SEQ ID NO: 35 (cellulose binding domain), SEQ ID NO: 36 (cellulose binding domain), SEQ ID NO: 37 (TNPGVSAWQVNTAYTAGQLVTYNGKTYKCLQPHTSLAGWEPSNVPALWQLQ), SEQ ID NO: 38 (GST-tag), and SEQ ID NO: 39 (MBP-tag).

The term "enzymatic cleavage site" denotes a sequence of amino acid residues connected to each other via peptides bonds that can specifically be cleaved by a protease. In one embodiment the protease is IgA-protease, Granzyme B, Tev protease, PreScission® protease, Thrombin, Faktor10a, IdeS protease, or Enterokinase.

The term "IgA-protease" denotes a protease derived from Neisseria gonorrhoeae with a recognition site comprising one of the following sequences wherein "↓" denotes the position of the cleaved bond:

Pro-Ala-Pro ↓ Ser-Pro, (SEQ ID NO: 40)

Pro-Pro ↓ Ser-Pro, (SEQ ID NO: 41)

Pro-Pro ↓ Ala-Pro, (SEQ ID NO: 42)

-continued

Pro-Pro ↓ Thr-Pro, (SEQ ID NO: 43)

Pro-Pro ↓ Gly-Pro, (SEQ ID NO: 44)

Pro-Arg-Pro-Pro ↓ Thr-Pro, (SEQ ID NO: 45)

Val-Val-Ala-Pro-Pro ↓ Ala-Pro, (SEQ ID NO: 46)

Val-Val-Ala-Pro-Pro ↓ Ser-Pro, (SEQ ID NO: 47)

Val-Val-Ala-Pro-Pro ↓ Thr-Pro, (SEQ ID NO: 48)

Val-Val-Ala-Pro-Pro ↓ Gly-Pro, (SEQ ID NO: 49)

Pro-Arg-Pro-Pro ↓ Thr-Pro, (SEQ ID NO: 50)

Ala-Pro-Pro-Ala ↓ Ala-Pro, (SEQ ID NO: 51)

Pro-Arg-Pro-Pro ↓ Ala-Pro, (SEQ ID NO: 52)

Pro-Arg-Pro-Pro ↓ Ser-Pro, (SEQ ID NO: 53)

Pro-Arg-Pro-Pro ↓ Gly-Pro. (SEQ ID NO: 54)

The term "linker" or "peptidic linker" as used within this application denotes peptide linkers of natural and/or synthetic origin. They consist of a linear amino acid chain wherein the 20 naturally occurring amino acids are the monomeric building blocks. The chain has a length of from 1 to 50 amino acids, preferred between 1 and 28 amino acids, especially preferred between 3 and 25 amino acids. The linker may contain repetitive amino acid sequences or sequences of naturally occurring polypeptides, such as polypeptides with a hinge-function. The linker has the function to ensure that a peptide conjugated to an anti-CD4 antibody can perform its biological activity by allowing the peptide to fold correctly and to be presented properly. Preferably the linker is a "synthetic peptidic linker" that is designated to be rich in glycine, glutamine, and/or serine residues. These residues are arranged e.g. in small repetitive units of up to five amino acids, such as GGGGS, QQQQG, or SSSSG. This small repetitive unit may be repeated for two to five times to form a multimeric unit. At the amino- and/or carboxy-terminal ends of the multimeric unit up to six additional arbitrary, naturally occurring amino acids may be added. Other synthetic peptidic linkers are composed of a single amino acid, which is repeated between 10 to 20 times and may comprise at the amino- and/or carboxy-terminal end up to six additional arbitrary, naturally occurring amino acids. All peptidic linkers can be encoded by a nucleic acid molecule and therefore can be recombinantly expressed.

Fusion Polypeptide as Reported Herein

It has been found that soluble Fc-receptors can be produced by expressing the Fc-receptor as fusion polypeptide with an Fc-region that does not substantially bind to the fused Fc-receptor.

The term "does not substantially bind to the Fc-receptor" denotes that the Fc-region to which the Fc-receptor is fused does not bind to the Fc-receptor to such an extent that aggregates are formed.

One aspect as reported herein is a fusion polypeptide according to formula I

R1-FC-R2 (formula I)

wherein
R1 denotes a first Fc-receptor,
R2 denotes a second Fc-receptor, and
FC denotes a heavy chain Fc-region polypeptide,
wherein R1 or R2 or both are present,
wherein FC does not substantially bind to R1 and/or R2.

One aspect as reported herein is a fusion polypeptide according to formula II

R1-CS1-L1-CS2-FC-CS3-L2-CS4-R2    (formula II)

wherein
R1 denotes a first Fc-receptor,
R2 denotes a second Fc-receptor,
FC denotes a heavy chain Fc-region polypeptide,
CS1 denotes a first cleavage site,
CS2 denotes a second cleavage site,
CS3 denotes a third cleavage site,
CS4 denotes a fourth cleavage site,
L1 denotes a first intervening amino acid sequence, and
L2 denotes a second intervening amino acid sequence,
wherein R1 or R2 or both are present,
wherein any one of CS1, CS2, CS3, CS4 can independently of each other be present or absent,
wherein L1 and L2 can independently of each other be present or absent,
wherein FC does not substantially bind to R1 and/or R2.

The Fc-receptors contained in the fusion polypeptide as reported herein can be any Fc-receptor from any species including but not limited to human, mouse, rat, rabbit, and monkey.

In one embodiment the Fc-receptor is selected from the group comprising Fcgamma-receptor and neonatal Fc-receptor. In one embodiment the Fc-receptor is human Fcgamma-receptor, human neonatal Fc-receptor, murine Fc-receptor, and rabbit neonatal Fc-receptor.

In one embodiment the human Fcgamma-receptor is selected from human FcγRI (CD64), human FcγRII (CD32), human FcγRIIA, human FcγRIIB, human FcγRIIC, human FcγRIII (CD16), human FcγRIIIA, and human FcγRIIIB.

In one embodiment the human neonatal Fc-receptor is human FcRn.

In one embodiment the murine Fc-receptor is selected from murine FcγRI (CD64), murine FcγRII (CD32), murine FcγRIIB, murine FcγRIII (CD16), murine FcγRIII-2 (CD16-2), and murine FcγRIV.

In one embodiment the FC is a variant of a heavy chain polypeptide selected from the group of human IgG heavy chain polypeptide, murine IgG heavy chain polypeptide, rabbit IgG heavy chain polypeptide.

In one embodiment the FC is a variant of a heavy chain polypeptide selected from the group of human IgG1 heavy chain polypeptide, human IgG2 heavy chain polypeptide, human IgG3 heavy chain polypeptide, human IgG4 heavy chain polypeptide, murine IgG1 heavy chain polypeptide, murine IgG2 heavy chain polypeptide, murine IgG2a heavy chain polypeptide, murine IgG3 heavy chain polypeptide, rabbit IgG heavy chain polypeptide.

As the Fc-region comprised in the fusion polypeptide as reported herein shall not substantially bind to any of the Fc-receptor(s) fused thereto.

In one embodiment the fusion polypeptide possesses substantially no effector functions, which make it a desirable candidate for applications in which certain effector functions are unnecessary or deleterious. In vitro and/or in vivo cytotoxicity assays can be conducted to confirm the reduction/depletion of effector functions. For example, Fc-receptor (FcR) binding assays can be conducted to ensure that the fusion polypeptide lacks FcγR binding (hence likely lacking ADCC activity). The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch, J. V. and Kinet, J. P., Annu Rev. Immunol. 9 (1991) 457-492. Non-limiting examples of in vitro assays to assess ADCC activity of a molecule of interest is described in U.S. Pat. No. 5,500,362 (see, e.g. Hellstrom, I. et al., Proc. Natl. Acad. Sci. USA 83 (1986) 7059-7063; and Hellstrom, I. et al., Proc. Natl. Acad. Sci. USA 82 (1985) 1499-1502); U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. FcRn binding and in vivo clearance/half-life determinations can also be performed using methods known in the art (see, e.g., Petkova, S. B. et al., Int. Immunol. 18 (2006: 1759-1769).

The affinities and binding properties of an Fc-region for its ligand, may be determined by a variety of in vitro assay methods (biochemical or immunological based assays) known in the art for determining Fc-region/FcR interactions, i.e., specific binding of an Fc-region to an FcγR including but not limited to, equilibrium methods (e.g. enzyme-linked immuno absorbent assay (ELISA) or radioimmunoassay (RIA)), or kinetics (e.g. BIACORE® analysis), and other methods such as indirect binding assays, competitive inhibition assays, fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, $4^{th}$ Ed., Lippincott-Raven, Philadelphia (1999).

In one embodiment FC is either an Fc-region of human origin of the subclass IgG4 or an Fc-region of human origin of the subclass IgG1, IgG2, or IgG3, which is modified in such a way that no Fcγ receptor (e.g. FcγRIIIa) binding. In one embodiment FC is an Fc-region of human origin, especially either from human IgG4 subclass or a mutated Fc-region from human IgG1 subclass. In one embodiment FC is of the human IgG1 subclass with mutations L234A and L235A. In one embodiment FC is of the human IgG4 subclass with mutation S228P. While IgG4 shows reduced Fcγ receptor (FcγRIIIa) binding, antibodies of other IgG subclasses show strong binding. However Pro238, Asp265, Asp270, Asn297 (loss of Fc carbohydrate), Pro329, Leu234, Leu235, Gly236, Gly237, Ile253, Ser254, Lys288, Thr307, Gln311, Asn434, or/and His435 are residues which, if altered, provide also reduced Fcγ receptor binding (Shields, R. L., et al., J. Biol. Chem. 276 (2001) 6591-6604; Lund, J., et al., FASEB J. 9 (1995) 115-119; Morgan, A., et al., Immunology 86 (1995) 319-324; EP 0 307 434). In one embodiment FC is in regard to Fcγ receptor binding of IgG4 subclass, or of IgG1 or IgG2 subclass, with a mutation in L234, L235, and/or D265, and/or contains the PVA236 mutation. In one embodiment FC comprises one or more of the mutations S228P, L234A, L235A, L235E, and/or PVA236 (PVA236 means that the amino acid sequence ELLG (given in one letter amino acid code) from amino acid position 233 to 236 of IgG1 or EFLG of IgG4 is replaced by PVA). In one embodiment the mutations are S228P for IgG4, and L234A and L235A for IgG1.

Fc-region binding sites are known in the state of the art and described e.g. by Lukas, T. J., et al., J. Immunol. 127 (1981) 2555-2560; Brunhouse, R. and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virol. 75 (2001) 12161-12168; Morgan, A., et al., Immunology 86 (1995) 319-324; and EP 0 307 434. Fc-region binding sites are, e.g., characterized by the amino acids L234, L235, D270, N297, E318, K320, K322, P331, and P329 (numbering according to EU index of Kabat).

Fc-regions with reduced effector function include those with substitution of one or more of Fc-region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DA" Fc mutant with substitution of residue 265 and the so-called "DANA" Fc mutant with substitution of residues 265 and 297 to alanine (U.S. Pat. No. 7,332,581).

Certain Fc-region variants with improved or diminished binding to FcRs are described. (See, e.g., U.S. Pat. No. 6,737,056; WO 2004/056312, and Shields, R. L. et al., J. Biol. Chem. 276 (2001) 6591-6604)

In some embodiments, alterations are made in the Fc-region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

See also Duncan, A. R. and Winter, G., Nature 322 (1988) 738-740; U.S. Pat. Nos. 5,648,260; 5,624,821; and WO 94/29351 concerning other examples of Fc region variants.

In one embodiment the heavy chain Fc-region polypeptide has an amino acid mutation at one or more of position 234, 235, 236, 237, 238, 239, 253, 254, 265, 266, 267, 268, 269, 270, 288, 297, 298, 299, 307, 311, 327, 328, 329, 330, 331, 332, 434, and 435. In one embodiment the one or more of the Fc-receptors is an Fc gamma receptor.

In one embodiment the human IgG1 heavy chain polypeptide has a mutation at one or more of amino acid positions 233, 234, 235, 236, 265, 297, 329, and 331.

In one embodiment the human IgG1 heavy chain polypeptide has one or more of the amino acid mutations E233P, L234A, L235A, L235E, AG236, D265A, N297A, N297D, P329A, P329G, and P331S.

In one embodiment the human IgG1 heavy chain polypeptide has the amino acid mutations L234A and L235A and one or more of E233P, L235E, AG236, D265A, N297A, N297D, P329A, P329G, and P331S.

In one embodiment the human IgG1 heavy chain polypeptide has the amino acid mutations L234A and L235A and P329A or P329G.

In one embodiment the human IgG2 heavy chain polypeptide has mutations at one or more of amino acid positions 233, 234, 235, 236, 265, and 329.

In one embodiment the human IgG4 heavy chain polypeptide has a mutation at one or more of amino acid positions 228, 235, 265, and 329.

In one embodiment the human IgG4 heavy chain polypeptide has one or more of the mutations S228P, L235E, P329A, and P329G.

In one embodiment the human IgG4 heavy chain polypeptide has the mutations S228P and L235E and P329A or P329G.

In one embodiment the heavy chain Fc-region polypeptide has an amino acid mutation at one or more of position 248, 250, 251, 252, 253, 254, 255, 256, 257, 272, 285, 288, 290, 291, 308, 309, 310, 311, 314, 385, 386, 387, 428, 433, 434, 435, and 436. In one embodiment the one or more of the Fc-receptors is an FcRn.

In one embodiment the human IgG heavy chain polypeptide has a mutation at one or more of the amino acid positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439, and/or 447.

In one embodiment the human IgG heavy chain polypeptide that has a reduced binding to FcRn has one or more amino acid alterations at the amino acid positions 252, 253, 254, 255, 288, 309, 386, 388, 400, 415, 433, 435, 436, 439, and/or 447.

The fusion polypeptide can comprise between the Fc-receptor and the Fc-region a linker polypeptide. This linker polypeptide can be used to adjust the distance between the Fc-receptor and the Fc-region to allow both regions to function in the intended way.

In one embodiment the linker polypeptide is selected from the group comprising (G3S)3, (G3S)4, (G3S)5, (G3S)6, (G4S)3, (G4S)4, (G4S)5, (G5S)2, (G5S)3, and (G5S)4 and any combination thereof.

Additionally, the fusion polypeptide can comprise between the Fc-receptor and the Fc-region a tag, e.g. suitable for affinity purification or immobilization.

In one embodiment the tag is selected from a the group comprising Arg-tag, Avi-tag, His-Avi-tag, His-tag, Flag-tag, 3xFlag-tag, Strep-tag, Nano-tag, SBP-tag, c-myc-tag, S-tag, calmodulin-binding-peptide, cellulose-binding-domain, chitin-binding-domain, GST-tag, MBP-tag, streptavidin or avidin, biotin, lectin, polysaccharide, steroid, steroid binding protein, hormone, and hormone receptor.

The linker polypeptide and the tag can be combined in an intervening amino acid sequence that is located between the Fc-receptor and the Fc-region.

In one embodiment the intervening amino acid sequence is selected from a first group comprising (G3S)3, (G3S)4, (G3S)5, (G3S)6, (G4S)3, (G4S)4, (G4S)5, (G5S)2, (G5S)3, and (G5S)4, or from a second group comprising Arg-tag, Avi-tag, His-Avi-tag, His-tag, Flag-tag, 3xFlag-tag, Strep-tag, Nano-tag, SBP-tag, c-myc-tag, S-tag, calmodulin-binding-peptide, cellulose-binding-domain, chitin-binding-domain, GST-tag, or MBP-tag, or from combinations of two elements of these group.

The intervening amino acid sequence can be located either before or after a cleavage site in the fusion polypeptide.

In one embodiment the cleavage site is an enzymatic cleavage site. In one embodiment the enzymatic cleavage site is selected from the group comprising IgA-protease protease cleavage site, Granzyme B protease cleavage site, Tev protease cleavage site, PreScission® protease cleavage site, Thrombin cleavage site, Faktor10a protease site, IdeS protease cleavage site, SUMO protease cleavage site and Enterokinase cleavage site. In one embodiment the cleavage site is selected from the group of IgA protease cleavage site, PreScission® protease cleavage site, granzyme B cleavage site, and IdeS protease cleavage site.

In one embodiment the fusion polypeptide comprises an inherent cleavage site of the protease papain, or the protease pepsin, or the IdeS protease.

One aspect as reported herein is a dimeric fusion polypeptide comprising two fusion polypeptides as reported herein.

As the fusion polypeptide as reported herein comprises an Fc-region which in turn comprises an immunoglobulin hinge region the dimeric fusion polypeptide comprises one or more disulfide bridges covalently linking the first fusion polypeptide with the second fusion polypeptide.

The dimeric fusion polypeptide can be a homodimeric fusion polypeptide or a heterodimeric fusion polypeptide.

Additionally the dimeric fusion polypeptide can comprise a first fusion polypeptide according to formula I $$R1\text{-}FC\text{-}R2 \qquad \text{(formula I)}$$

wherein
R1 denotes a first Fc-receptor,
R2 denotes a second Fc-receptor, and
FC denotes a heavy chain Fc-region polypeptide,
wherein R1 or R2 or both are present,
wherein FC does not substantially bind to R1 and/or R2, or according to formula II $$R1\text{-}CS1\text{-}L1\text{-}CS2\text{-}FC\text{-}CS3\text{-}L2\text{-}CS4\text{-}R2 \qquad \text{(formula II)}$$

wherein
R1 denotes a first Fc-receptor,
R2 denotes a second Fc-receptor,
FC denotes a heavy chain Fc-region polypeptide,
CS1 denotes a first cleavage site,
CS2 denotes a second cleavage site,
CS3 denotes a third cleavage site,
CS4 denotes a fourth cleavage site,
L1 denotes a first intervening amino acid sequence, and
L2 denotes a second intervening amino acid sequence,
wherein R1 or R2 or both are present,
  wherein any one of CS1, CS2, CS3, CS4 can independently of each other be present or absent,
  wherein L1 and L2 can independently of each other be present or absent,
wherein FC does not substantially bind to R1 and/or R2, wherein the first and the second fusion polypeptide of the dimeric fusion polypeptide can be selected independently of each other from formula I and formula II.

If the dimeric fusion polypeptide can comprises two different fusion polypeptides a mechanism to ensure the heterodimerization has to be used.

In one embodiment the first FC comprises the mutation T366W and optionally the mutation S354C and the second FC comprises the mutations T366S, L368A and Y407V and optionally the mutation Y349C.

In one embodiment the fusion polypeptide is characterized in that
  a) R1 and R2 of the first and second polypeptide are identical,
  b) R1 and R2 of the first fusion polypeptide are identical, R1 and R2 of the second fusion polypeptide are identical but different from R1 and R2 of the first fusion polypeptide,
  c) R1 of the first and second fusion polypeptide are identical and R2 of the first and second fusion polypeptide are identical but different from R1,
  d) R1 of the first and second fusion polypeptide are identical and both R2 are absent,
  e) R1 of the first and second fusion polypeptide are different and both R2 are absent,
  f) R2 of the first and second fusion polypeptide are identical and both R1 are absent,
  g) R2 of the first and second fusion polypeptide are different and both R1 are absent,
  h) R1 of the first fusion polypeptide and R2 of the second polypeptide are different and R2 of the first fusion polypeptide is absent and R1 of the second polypeptide is absent.

Applications of the Fusion Polypeptide as Reported Herein

One aspect as reported herein is the use of an immobilized fusion polypeptide as reported herein as affinity chromatography ligand.

In one embodiment the fusion polypeptide is bound to a solid phase. In one embodiment the solid phase is a chromatography material. In one embodiment the fusion polypeptide is biotinylated and the solid phase is derivatized with streptavidin.

In one embodiment the fusion polypeptide comprises a cleavage site between the Fc-receptor and the Fc-region. In one embodiment the fusion polypeptide is cleaved prior to biotinylation.

In one embodiment the fusion polypeptide comprises an immobilization tag between the Fc-receptor and the cleavage site. In one embodiment the immobilization tag is a His-Avi-tag.

Also reported is an affinity chromatography column that comprises a matrix and matrix bound chromatographical functional groups, characterized in that the matrix bound chromatographical functional group comprises a fusion polypeptide as reported herein.

In one embodiment the fusion polypeptide comprises a cleavage site between the Fc-receptor and the Fc-region. In one embodiment the fusion polypeptide is cleaved prior to biotinylation.

In one embodiment the fusion polypeptide comprises an immobilization tag between the Fc-receptor and the cleavage site. In one embodiment the immobilization tag is an Avi-tag.

One aspect as reported herein is the use of an immobilized fusion polypeptide as reported herein for determining the Fc-receptor binding of an antibody.

In one embodiment the antibody is a low affinity antibody.

In one embodiment the determining is by surface plasmon resonance. In one embodiment the antibody is captured by a monomeric Fc-receptor. In one embodiment the antibody is captured by a dimeric antibody.

Recombinant Methods

One aspect as reported herein is a method for the production of a soluble Fc-receptor comprising the following steps
  a) cultivating a cell comprising a nucleic acid encoding a fusion polypeptide as reported herein,
  b) recovering the fusion polypeptide from the cell or the cultivation medium,
  c) optionally cleaving the fusion polypeptide with a protease,
and thereby producing a soluble Fc-receptor.

Methods and techniques known to a person skilled in the art, which are useful for carrying out the current invention, are described e.g. in Ausubel, F. M., ed., Current Protocols in Molecular Biology, Volumes I to III (1997), Wiley and Sons; Sambrook et al., Molecular Cloning: A Laboratory Manual, Second Edition, Cold Spring Harbor Laboratory Press, Cold Spring Harbor, N.Y. (1989).

The nucleic acid encoding the fusion polypeptide as reported herein can be expressed in a host cell. After recombinant expression the fusion polypeptide can be purified by methods known to a person skilled in the art. These methods are well established and widespread used for immunoglobulin purification and are employed either alone or in combination. Such methods are, for example, affinity chromatography using microbial-derived proteins (e.g. protein A or protein G affinity chromatography), ion exchange chromatography (e.g. cation exchange (carboxymethyl resins), anion exchange (amino ethyl resins) and mixed-mode exchange chromatography), thiophilic adsorption (e.g. with beta-mercaptoethanol and other SH ligands), hydrophobic interaction or aromatic adsorption chromatography (e.g. with phenyl-Sepharose®, aza-arenophilic resins, or m-aminophenylboronic acid), metal chelate affinity chromatography (e.g. with Ni(II)- and Cu(II)-affinity material), size exclusion chromatography, and preparative electrophoretic methods (such as gel electrophoresis, capillary electrophoresis) (Vijayalakshmi, M. A., Appl. Biochem. Biotech. 75 (1998) 93-102). Prior to chromatographic purification or after the chromatographic purification the fusion polypeptide can enzymatically be cleaved in order to liberate the Fc-receptor. Expression cassettes comprise a promoter, a DNA segment encoding a secretion signal sequence, the structural gene, and a terminator/polyadenylation signal. The elements are assembled in an operatively linked form either on one plasmid encoding all required different fusion polypeptides, or on two or more plasmids each encoding one fusion polyp eptide. For the expression of the structural genes the plasmid(s) is (are) introduced into a suitable host cell. Proteins are produced in mammalian cells such as CHO cells, NS0 cells, Sp2/0 cells, COS cells, HEK cells, K562 cells, BHK cells, PER.C6® cells, and the like. In one embodiment the fusion polypeptide is expressed in a CHO cell, or a BHK cell, or a HEK cell. The regulatory elements of the plasmid have to be selected in a way that they are functional in the selected host cell. The expressed fusion polypeptides are functionally assembled.

An "expression plasmid" is a nucleic acid providing all required elements for the expression of the comprised structural gene(s) in a host cell. Typically, an expression plasmid comprises a prokaryotic plasmid propagation unit, e.g. for $E. coli$, comprising an origin of replication, and a selectable marker, an eukaryotic selection marker, and one or more expression cassettes for the expression of the structural gene(s) of interest each comprising a promoter, a structural gene, and a transcription terminator including a polyadenylation signal. Gene expression is usually placed under the control of a promoter, and such a structural gene is said to be "operably linked to" the promoter. Similarly, a regulatory element and a core promoter are operably linked if the regulatory element modulates the activity of the core promoter.

Antibodies may be produced using recombinant methods and compositions, e.g., as described in U.S. Pat. No. 4,816,567. In one embodiment, isolated nucleic acid encoding a fusion polypeptide antibody described herein is provided. In one embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising a first fusion polypeptide and an amino acid sequence comprising a second fusion polypeptide, or (2) a first vector comprising a nucleic acid that encodes an amino acid sequence comprising a first fusion polypeptide and a second vector comprising a nucleic acid that encodes an amino acid sequence comprising a second fusion polypeptide. In one embodiment, the host cell is eukaryotic, e.g. a Chinese Hamster Ovary (CHO) cell or lymphoid cell (e.g., Y0, NS0, Sp20 cell). In one embodiment, a method of making a fusion polypeptide is provided, wherein the method comprises culturing a host cell comprising a nucleic acid encoding the fusion polypeptide, as provided above, under conditions suitable for expression of the fusion polypeptide, and optionally recovering the fusion polypeptide from the host cell (or host cell culture medium).

For recombinant production of a fusion polypeptide as reported herein, nucleic acid encoding an fusion polypeptide, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the fusion polypeptide).

Suitable host cells for cloning or expression of fusion polypeptide-encoding vectors include prokaryotic or eukaryotic cells described herein. For example, fusion polypeptide may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523 (see also Charlton, K. A., In: Methods in Molecular Biology, Vol. 248, Lo, B. K. C. (ed.), Humana Press, Totowa, N. J. (2003), pp. 245-254, describing expression of antibody fragments in $E. coli$.). After expression, the fusion polypeptide may be isolated from the bacterial cell paste in a soluble fraction and can be further purified.

In addition to prokaryotes, eukaryotic microbes such as filamentous fungi or yeast are suitable cloning or expression hosts for fusion polypeptide-encoding vectors, including fungi and yeast strains whose glycosylation pathways have been "humanized," resulting in the production of a fusion polypeptide with a partially or fully human glycosylation pattern (see Gerngross, T. U., Nat. Biotech. 22 (2004) 1409-1414; and Li, H. et al., Nat. Biotech. 24 (2006) 210-215).

Suitable host cells for the expression of glycosylated fusion polypeptide are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts (see, e.g., U.S. Pat. Nos. 5,959,177, 6,040,498, 6,420,548, 7,125,978, and 6,417,429 (describing PLANTIBODIES™ technology for producing antibodies in transgenic plants)).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P., et al., Annals N.Y. Acad. Sci. 383 (1982) 44-68; MRC 5 cells; and FS4 cells. Other useful mammalian host cell lines include Chinese hamster ovary (CHO) cells, including DHFR⁻ CHO cells (Urlaub, G., et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

Methods and Compositions for Diagnostics and Detection

In certain embodiments, any of the fusion polypeptides provided herein is useful for detecting the presence of Fc-region containing molecules in a biological sample. The term "detecting" as used herein encompasses quantitative or qualitative detection.

In one embodiment, a fusion polypeptide as reported herein for use in a method of diagnosis or detection is provided. In a further aspect, a method of detecting the presence of Fc-region containing molecules in a biological sample is provided. In certain embodiments, the method comprises contacting the biological sample with a fusion polypeptide as reported herein under conditions permissive for binding of the fusion polypeptide to an Fc-region containing molecule, and detecting whether a complex is formed between the fusion polypeptide and an Fc-region containing molecule. Such method may be an in vitro or in vivo method.

In certain embodiments, labeled fusion polypeptides are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Pharmaceutical Compositions

Pharmaceutical compositions of a fusion polypeptide as reported herein are prepared by mixing such fusion polypeptide having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the fusion polypeptide, which matrices are in the form of shaped articles, e.g. films, or microcapsules.

The formulations to be used for in vivo administration are generally sterile. Sterility may be readily accomplished, e.g., by filtration through sterile filtration membranes.

Therapeutic Methods and Compositions

Any of the fusion polypeptides as reported herein may be used in therapeutic methods.

In one aspect, a fusion polypeptide for use as a medicament is provided. In further aspects, a fusion polypeptide for use in treating a disease characterized in elevated antibody levels is provided. In one embodiment the disease is an autoimmune disease. In certain embodiments, a fusion polypeptide for use in a method of treatment is provided. In certain embodiments, the invention provides a fusion polypeptide for use in a method of treating an individual having disease characterized in elevated antibody levels comprising administering to the individual an effective amount of the fusion polypeptide. In one such embodiment, the method further comprises administering to the individual an effective amount of at least one additional therapeutic agent. In further embodiments, the invention provides a fusion polypeptide for use in lowering antibody levels. In certain embodiments, the invention provides a fusion polypeptide for use in a method of lowering antibody levels in an individual comprising administering to the individual an effective of the fusion polypeptide to lower antibody levels. An "individual" according to any of the above embodiments is preferably a human.

In a further aspect, the invention provides for the use of a fusion polypeptide in the manufacture or preparation of a medicament. In one embodiment, the medicament is for treatment of a disease characterized in elevated antibody levels. In one embodiment the disease is an autoimmune disease. In a further embodiment, the medicament is for use in a method of treating elevated antibody levels comprising administering to an individual having a disease characterized in elevated antibody levels an effective amount of the medicament. In one such embodiment, the method further comprises administering to the individual an effective amount of at least one additional therapeutic agent. In a further embodiment, the medicament is for lowering antibody levels. In a further embodiment, the medicament is for use in a method of lowering antibody levels in an individual comprising administering to the individual an amount effective of the medicament to lower antibody level. An "individual" according to any of the above embodiments may be a human.

In a further aspect, the invention provides a method for treating a disease characterized in elevated antibody levels. In one embodiment the disease is an autoimmune disease. In one embodiment, the method comprises administering to an individual having such a disease characterized in elevated antibody levels an effective amount of a fusion polypeptide. In one such embodiment, the method further comprises administering to the individual an effective amount of at least one additional therapeutic agent. An "individual" according to any of the above embodiments may be a human.

In a further aspect, the invention provides a method for lowering antibody levels in an individual. In one embodiment, the method comprises administering to the individual an effective amount of a fusion polypeptide to lower antibody levels. In one embodiment, an "individual" is a human.

In a further aspect, the invention provides pharmaceutical compositions comprising any of the fusion polypeptides as reported herein, e.g., for use in any of the above therapeutic methods. In one embodiment, a pharmaceutical composition comprises any of the fusion polypeptides as reported herein and a pharmaceutically acceptable carrier. In another embodiment, a pharmaceutical composition comprises any of the fusion polypeptides as reported herein and at least one additional therapeutic agent.

Fusion polypeptides of the invention can be used either alone or in combination with other agents in a therapy. For instance, a fusion polypeptide of the invention may be co-administered with at least one additional therapeutic agent.

Such combination therapies noted above encompass combined administration (where two or more therapeutic agents are included in the same or separate formulations), and separate administration, in which case, administration of the fusion polypeptide of the invention can occur prior to, simultaneously, and/or following, administration of the additional therapeutic agent and/or adjuvant.

A fusion polypeptide of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Fusion polypeptides of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The fusion polypeptide need not be, but is optionally formulated with one or more agents currently used to prevent or treat the disorder in question. The effective amount of such other agents depends on the amount of fusion polypeptide present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a fusion polypeptide of the invention (when used alone or in combination with one or more other additional therapeutic agents) will depend on the type of disease to be treated, the type of fusion polypeptide, the severity and course of the disease, whether the fusion polypeptide is administered for preventive or therapeutic purposes, previous therapy, the patient's clinical history and response to the fusion polypeptide, and the discretion of the attending physician. The fusion polypeptide is suitably administered to the patient at one time or over a series of treatments. Depending on the type and severity of the disease, about 1 μg/kg to 15 mg/kg (e.g. 0.5 mg/kg-10 mg/kg) of fusion polypeptide can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the fusion polypeptide would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the fusion polypeptide). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to a fusion polyp eptide.

Articles of Manufacture

In another aspect of the invention, an article of manufacture containing materials useful for the treatment, prevention and/or diagnosis of the disorders described above is provided. The article of manufacture comprises a container and a label or package insert on or associated with the container.

Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a fusion polypeptide of the invention. The label or package insert indicates that the composition is used for treating the condition of choice. Moreover, the article of manufacture may comprise (a) a first container with a composition contained therein, wherein the composition comprises a fusion polypeptide of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to a fusion polypeptide.

The following examples, figures and sequences are provided to aid the understanding of the present invention, the true scope of which is set forth in the appended claims. It is understood that modifications can be made in the procedures set forth without departing from the spirit of the invention.

EXAMPLES

Example 1

Generation of the Expression Plasmids a) Generation of the Expression Plasmid for an FcgammaRIIIaV158-Avi-IgA Protease-Fc LALA P239G Fusion Polypeptide The FcgammaRIIIaV158-Avi-IgA Protease-Fc LALA P239G fusion polypeptide encoding gene was assembled by fusing chemically synthesized DNA fragments coding i) for a murine immunoglobulin heavy chain signal sequence (MGWSCIILFLVATATGVHS: SEQ ID NO: 55), ii) a human Fc gamma receptor IIIa V158 from amino acid residues 2-193 (i.e. excluding the starting methionine), and iii) a human Fc-gamma-1-heavy chain constant region (hinge-CH2-CH3) with the mutations L234A, L235A and P329G.

The expression plasmid for the transient expression of an FcgammaRIIIaV158-Avi-IgA Protease-Fc LALA P239G fusion polypeptide in HEK293 cells comprised besides the FcgammaRIIIaV158-Avi-IgA Protease-Fc LALA P239G fusion polypeptide expression cassette an origin of replication from the vector pUC18 which allows replication of this plasmid in *E. coli*, and a beta-lactamase gene which confers ampicillin resistance in *E. coli*. In detail, the transcription unit of the FcgammaRIIIaV158-Avi-IgA Protease-Fc LALA P239G fusion polypeptide encoding gene comprises the following functional elements:

the immediate early enhancer and promoter from the human cytomegalovirus (P-CMV) including intron A, a human heavy chain immunoglobulin 5'-untranslated region (5'UTR), a murine immunoglobulin heavy chain signal sequence, a soluble human Fc gamma receptor III V158 polypeptide from amino acid position 2-193 of the wild-type human Fc gamma receptor III V158 protein, a human Fc-gamma-1-heavy chain constant region (hinge-CH2-CH3, LALA P329G), and the bovine growth hormone polyadenylation sequence (BGH poly A signal sequence).

The amino acid sequence of the mature FcgammaRIIaV158-Avi-IgA Protease-Fc LALA P239G fusion polypeptide is:

```
                                            (SEQ ID NO: 56)
GMRTEDLPKA VVFLEPQWYR VLEKDSVTLK CQGAYSPEDN

STQWFHNESL ISSQASSYFI DAATVDDSGE YRCQTNLSTL

SDPVQLEVHI GWLLLQAPRW VFKEEDPIHL RCHSWKNTAL

HKVTYLQNGK GRKYFHHNSD FYIPKATLKD SGSYFCRGLV

GSKNVSSETV NITITQGLAV STISSFFPPG YQGLNDIFEA

QKIEWHELVV APPAPEDKTH TCPPCPAPEA AGGPSVFLFP

PKPKDTLMIS RTPEVTCVVV DVSHEDPEVK FNWYVDGVEV

HNAKTKPREE QYNSTYRVVS VLTVLHQDWL NGKEYKCKVS

NKALGAPIEK TISKAKGQPR EPQVYTLPPS RDELTKNQVS

LTCLVKGFYP SDIAVEWESN GQPENNYKTT PPVLDSDGSF

FLYSKLTVDK SRWQQGNVFS CSVMHEALHN HYTQKSLSLS

PGK.
```

The following fusion polypeptides can be obtained analogously:

FcgammaRIIa-LR(H131)-Avi-IgA Protease-Fc LALA P239G fusion polypeptide:

```
                                            (SEQ ID NO: 57)
QAAAPPKAVL KLEPPWINVL QEDSVTLTCQ GARSPESDSI

QWFHNGNLIP THTQPSYRFK ANNNDSGEYT CQTGQTSLSD

PVHLTVLSEW LVLQTPHLEF QEGETIMLRC HSWKDKPLVK

VTFFQNGKSQ KFSHLDPTFS IPQANHSHSG DYHCTGNIGY

TLFSSKPVTI TVQVPSMGSS SPMGIGLNDI FEAQKIEWHE

LVVAPPAPED KTHTCPPCPA PEAAGGPSVF LFPPKPKDTL

MISRTPEVTC VVVDVSHEDP EVKFNWYVDG VEVHNAKTKP

REEQYNSTYR VVSVLTVLHQ DWLNGKEYKC KVSNKALGAP

IEKTISKAKG QPREPQVYTL PPSRDELTKN QVSLTCLVKG

FYPSDIAVEW ESNGQPENNY KTTPPVLDSD GSFFLYSKLT

VDKSRWQQGN VFSCSVMHEA LHNHYTQKSL SLSPGK.
```

FcgammaRIIb-Avi-IgA Protease-Fc LALA P239G fusion polypeptide:

```
                                       (SEQ ID NO: 58)
APPKAVLKLE  PQWINVLQED  SVTLTCRGTH  SPESDSIQWF

HNGNLIPTHT  QPSYRFKANN  NDSGEYTCQT  GQTSLSDPVH

LTVLSEWLVL  QTPHLEFQEG  ETIVLRCHSW  KDKPLVKVTF

FQNGKSKKFS  RSDPNFSIPQ  ANHSHSGDYH  CTGNIGYTLY

SSKPVTITVQ  APGLNDIFEA  QKIEWHELVV  APPAPEDKTH

TCPPCPAPEA  AGGPSVFLFP  PKPKDTLMIS  RTPEVTCVVV

DVSHEDPEVK  FNWYVDGVEV  HNAKTKPREE  QYNSTYRVVS

VLTVLHQDWL  NGKEYKCKVS  NKALGAPIEK  TISKAKGQPR

EPQVYTLPPS  RDELTKNQVS  LTCLVKGFYP  SDIAVEWESN

GQPENNYKTT  PPVLDSDGSF  FLYSKLTVDK  SRWQQGNVFS

CSVMHEALHN  HYTQKSLSLS  PGK.
```

FcgammaRIIIb-Avi-IgA Protease-Fc LALA P239G fusion polypeptide:

```
                                       (SEQ ID NO: 59)
GMRTEDLPKA  VVFLEPQWYS  VLEKDSVTLK  CQGAYSPEDN

STQWFHNESL  ISSQASSYFI  DAATVNDSGE  YRCQTNLSTL

SDPVQLEVHI  GWLLLQAPRW  VFKEEDPIHL  RCHSWKNTAL

HKVTYLQNGK  DRKYFHHNSD  FHIPKATLKD  SGSYFCRGLV

GSKNVSSETV  NITITQGLAV  STISSFSPPG  YQGLNDIFEA

QKIEWHELVV  APPAPEDKTH  TCPPCPAPEA  AGGPSVFLFP

PKPKDTLMIS  RTPEVTCVVV  DVSHEDPEVK  FNWYVDGVEV

HNAKTKPREE  QYNSTYRVVS  VLTVLHQDWL  NGKEYKCKVS

NKALGAPIEK  TISKAKGQPR  EPQVYTLPPS  RDELTKNQVS

LTCLVKGFYP  SDIAVEWESN  GQPENNYKTT  PPVLDSDGSF

FLYSKLTVDK  SRWQQGNVFS  CSVMHEALHN  HYTQKSLSLS

PGK.
``` minimal FcgammaRIIIa-Avi-Fc LALA p239G fusion polypeptide (without protease cleavage site):

```
                                       (SEQ ID NO: 60)
GWLLLQAPRW  VFKEEDPIHL  RCHSWKNTAL  HKVTYLQNGK

GRKYFHHNSD  FYIPKATLKD  SGSYFCRGLV  GSKNVSSETV

NITITQGLAV  STISSFPPPG  YQGLNDIFEA  QKIEWHELED

KTHTCPPCPA  PEAAGGPSVF  LFPPKPKDTL  MISRTPEVTC

VVVDVSHEDP  EVKFNWYVDG  VEVHNAKTKP  REEQYNSTYR

VVSVLTVLHQ  DWLNGKEYKC  KVSNKALGAP  IEKTISKAKG

QPREPQVYTL  PPSRDELTKN  QVSLTCLVKG  FYPSDIAVEW

ESNGQPENNY  KTTPPVLDSD  GSFFLYSKLT  VDKSRWQQGN

VFSCSVMHEA  LHNHYTQKSL  SLSPGK.
``` c) Generation of the "Knob-into-hole" Expression Plasmids for Dimeric Fc-receptor Fusion Polypeptide The expression plasmid for the transient expression of the Fc-receptor Fc-region fusion polypeptide (hole) in HEK293 cells was derived from the expression vector described above under item a). It differentiated therefrom in the DNA sequence coding for the Fc-region with hole mutations T366S, L368A, Y407V, and Y349C within the human gamma-1 heavy chain constant region.

The expression plasmid for the transient expression of the Fc-receptor Fc-region fusion polypeptide (knob) in HEK293 cells was derived from the expression vector described above under item a). It differentiated therefrom in the DNA sequence coding for the Fc-region with knob mutations T366W and S354C within the human gamma-1 heavy chain constant region.

The expression plasmid for the transient expression of the Fc-receptor Fc-region fusion polypeptide (knob/hole) in HEK293 comprised besides the fusion polypeptide (knob/hole) expression cassette an origin of replication from the vector pUC18 which allows replication of this plasmid in *E. coli*, and a beta-lactamase gene which confers ampicillin resistance in *E. coli*. In detail, the transcription unit of the fusion polypeptide (knob/hole) encoding gene comprises the following functional elements:

- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- a human Fc-gamma-1-heavy chain constant region (hinge-CH2-CH3) with the hole mutations T366S, L368A, Y407V, and Y349C or the knob mutations T366W and S354C within the human gamma-1 heavy chain constant region, and
- the bovine growth hormone polyadenylation sequence (BGH poly A signal sequence).

Example 2

Transient Expression, Purification and Analytical Characterization of the FcgammaRIIIaV158-Avi-IgA Protease-Fc LALA P239G Fusion Polypeptide The fusion polypeptides were obtained by transient transfection of HEK293 cells (human embryonic kidney cell line 293-derived) cultivated in F17 Medium (Invitrogen Corp.). For transfection "293-Free" Transfection Reagent (Novagen) was used. The knob-into-hole fusion polypeptide pairs were expressed from two different plasmids using an equimolar plasmid ratio upon transfection. Transfections were performed as specified in the manufacturer's instructions. Fusion polypeptide-containing cell culture supernatants were harvested seven days after transfection. Supernatants were stored at reduced temperature until purification.

General information regarding the recombinant expression of human immunoglobulins in e.g. HEK293 cells is given in: Meissner, P., et al., Biotechnol. Bioeng. 75 (2001) 197-203.

The fusion polypeptide-containing culture supernatants were filtered and purified by two chromatographic steps. The fusion polypeptides were captured by affinity chromatography using HiTrap MabSelect SuRe® (GE Healthcare) equilibrated with PBS (1 mM $KH_2PO_4$, 10 mM $Na_2HPO_4$, 137 mM NaCl, 2.7 mM KCl), pH 7.4. Unbound proteins were removed by washing with equilibration buffer, and the fusion polypeptide was recovered with 0.05 M citrate buffer, pH 3, immediately after elution neutralized to pH 6.5 with 1 M Tris-base, pH 9.0. Size exclusion chromatography on Superdex 200™ (GE Healthcare) was used as second purification step. The size exclusion chromatography was performed in 2 mM MOPS buffer, 0.125 M NaCl, pH 7.2. The eluted fusion polypeptides were concentrated with an Ultrafree-CL centrifugal filter unit equipped with a Biomax-SK membrane (Millipore, Billerica, Mass.) and stored at −80° C.

Four different FcgammaRIIIa-Fc fusion polypeptides were purified according to this protocol:
  a) FcgammaRIIIaV158-Avi-Fc LALA P239G (without cleavage site)
  b) minimal FcgammaRIIIaV158-Avi-Fc LALA P239G (without cleavage site)
  c) FcgammaRIIIaV158-Avi-PreScission® Protease(PP)-Fc LALA P239G
  d) FcgammaRIIIaV158-Avi-IgA Protease-Fc LALA P239G The protein concentrations of the fusion polypeptides were determined by measuring the optical density (OD) at 280 nm, using the molar extinction coefficient calculated on the basis of the amino acid sequence. Purity and proper dimer formation of fusion polypeptides were analyzed by SDS-PAGE in the presence and absence of a reducing agent (5 mM 1. 4-dithiothreitol) and staining with Coomassie® brilliant blue. Aggregate content of the fusion polypeptide preparations was determined by high-performance SEC using a Superdex 200™ analytical size-exclusion column (GE Healthcare). The integrity of the amino acid backbone of reduced fusion polypeptide was verified by Nano Electrospray QTOF mass spectrometry after removal of N-glycans by enzymatic treatment with a combination of neuraminidase, O-glycanase and peptide-N-glycosidase F (Roche Applied Science).

Example 3

Cleavage by Papain

Figure 2:
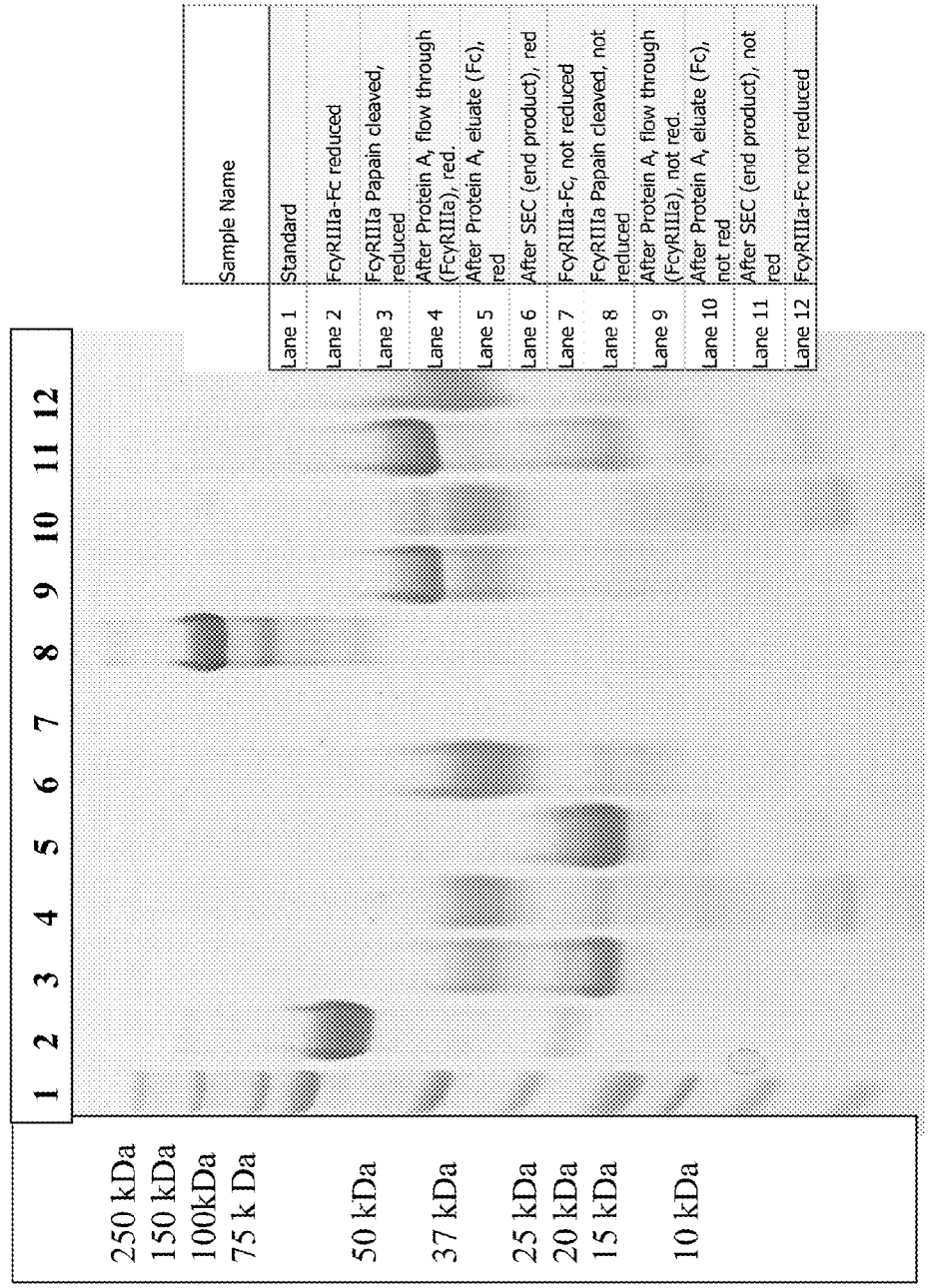
FIG. 2 Analytical SDS-PAGE gel of papain cleavage.

FcgammaRIIIa-Fc fusion polypeptides which do not comprise an enzymatic cleavage site can be cleaved by Papain. FcgammaRIIIa-Fc fusion polypeptide was cleaved by adding cysteine and 0.1 mU/mg fusion polypeptide Papain (from *Carica papaya*, Roche Diagnostics GmbH) at 37° C. for 1 h. Subsequent purification was done as described in Example 2. An analytical SDS-PAGE gel is shown in FIG. 2.

Example 4

Cleavage by IdeS Protease

Cleavage of the FcgammaRIIIaV158-Avi-Fc LALA P239G fusion polypeptide with IdeS protease is very inefficient and therefore in this case not useful.

Example 5

Cleavage by PreScission® Protease

After dialysis against 50 mM Tris, 150 NaCl, 1 mM EDTA, 1 mM DTT pH 7.4 FcgammaRIIIa-(PP)-Fc fusion polypeptide was cleaved by adding between 1-15 U PreScission® protease (GE Healthcare)/100 μg fusion polypeptide at room temperature overnight. Only part of the protein could be cleaved. On the other hand unspecific cleavage by PreScission® protease of receptor without PP cleavage site was observed.

Example 6

Cleavage by IgA Protease

Figure 3:
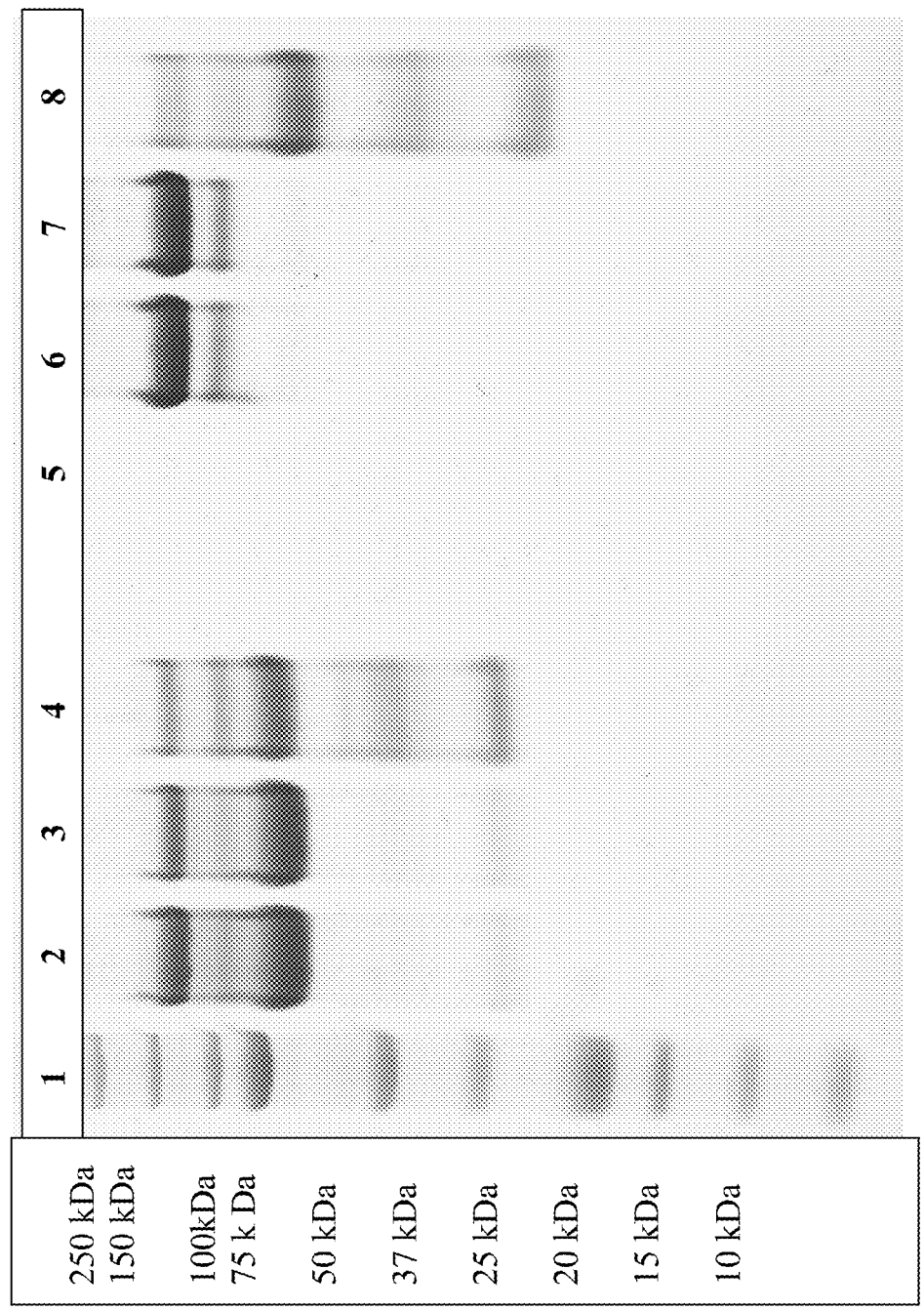

After dialysis against 50 mM Tris pH 8 using a Slide-a-lyzer dialysis cassette FcgammaRIIIa-Fc fusion polypeptide was cleaved by adding IgA Protease (Roche Diagnostics GmbH) at a ratio of w(protease)/w(fusion polypeptide) 1:100 at 21° C. overnight. Cleavage was controlled by analytical size exclusion chromatography (SEC, Superdex 75; GE Healthcare). After cleavage, the FcgammaRIIIa receptor was separated from IgA protease by preparative size exclusion chromatography on Superdex 75™ (GE Healthcare) and from Fc-Tag by HiTrap MabSelect SuRe® (GE Healthcare) column. An analytical SDS-Page gel is shown in FIG. 3.

TABLE

Yield of fermentation and purification of different FcgammaRIIIa V158 comprising fusion polypeptides.

| fusion polypeptide | molecular weight [kDa] | yield after capturing [mg/l supernatant] | monomer content (SEC) [%] | yield after SEC [mg/l supernatant] | yield after cleavage and further purification [mg/l supernatant] |
|---|---|---|---|---|---|
| FcgammaRIIIa V158-HisAvi (201) | 25.4 | 3.5 | 70 | 1.4 | — |
| FcgammaRIIIa V158-Avi-Fc LALA P329G (0.51) | 39 | 14 | 70 | 3 (not active) | |
| FcgammaRIIIa V158-Avi-Fc LALA P329G (0.51) | 49 | 80 | 95 | 78 | 21 (without Avi-tag) |
| FcgammaRIIIa V158-Avi-PP-Fc LALA P329G (0.51) | 50 | 24 | 50 | not determined | not determined |
| FcgammaRIIIa V158-Avi-IgAP-Fc LALA P329G (9.21) | 50 | 46 | 90 | 36 | 16 (with Avi-tag) |

Example 7

Preparation of FcgammaRIIIaV158 Affinity Column

An affinity column with FcgammaRIIIaV158 was prepared by in vitro biotinylation of the Avi-tag and subsequent coupling to Streptavidin Sepharose®. This can be done with the intact fusion polypeptide as well as with the receptor after having cleaved off the Fc-region. It is a very quick and efficient method for preparing an affinity column for analytical and preparative purposes.

Biotinylation of Receptor

A soluble extracellular domain of FcgammaRIIIaV158 with Avi Tag expressed in HEK293 cells was biotinylated after purification according to the following protocol: between 1.2 and 12 mg FcgammaRIIIaV158 or between 2.4 and 24 mg FcgammaRIIIaV158 Fc-region fusion polypeptide tagged in 2 mM MOPS, 125 mM NaCl pH 7.2, 0.02% Tween™, and 1 tablet Complete protease inhibitor (Roche) in 3 ml PBS were biotinylated using the biotinylation kit from Avidity according to the manufacturer instructions. Biotinylation reaction was done at room temperature overnight. The modified polypeptide was dialyzed against 20 mM sodium phosphate buffer, 150 mM NaCl pH 7.5 at 4° C. overnight to remove excess biotin.

Coupling to Streptavidin Sepharose®

1 g streptavidin Sepharose® (GE Healthcare) was added to the biotinylated and dialyzed receptor, incubated for 2 hours while shaking and finally filled in a 1 ml XK column (GE Healthcare).

Example 8

Chromatography Methods
General Conditions:
Equilibration buffer A: 20 mM Citric acid/150 mM NaCl pH 6.0
Elution buffer B: 20 mM Citric acid/150 mM NaCl pH 3.0
Elution: 5 min 100% A
  in 60 min to 100% B,
  0.1 min 100% B,
  6 min 100% A
Sample amount: 50 μg or more
Separation of Fucosylated and Afucosylated Antibodies Chromatography of antibodies on FcgRIIIa column allows to quantitate the completely fucosylated and the afucosylated fraction of the antibody. The afucosylated fraction of the antibody is correlated to ADCC of the antibody preparation.

Figure 4:
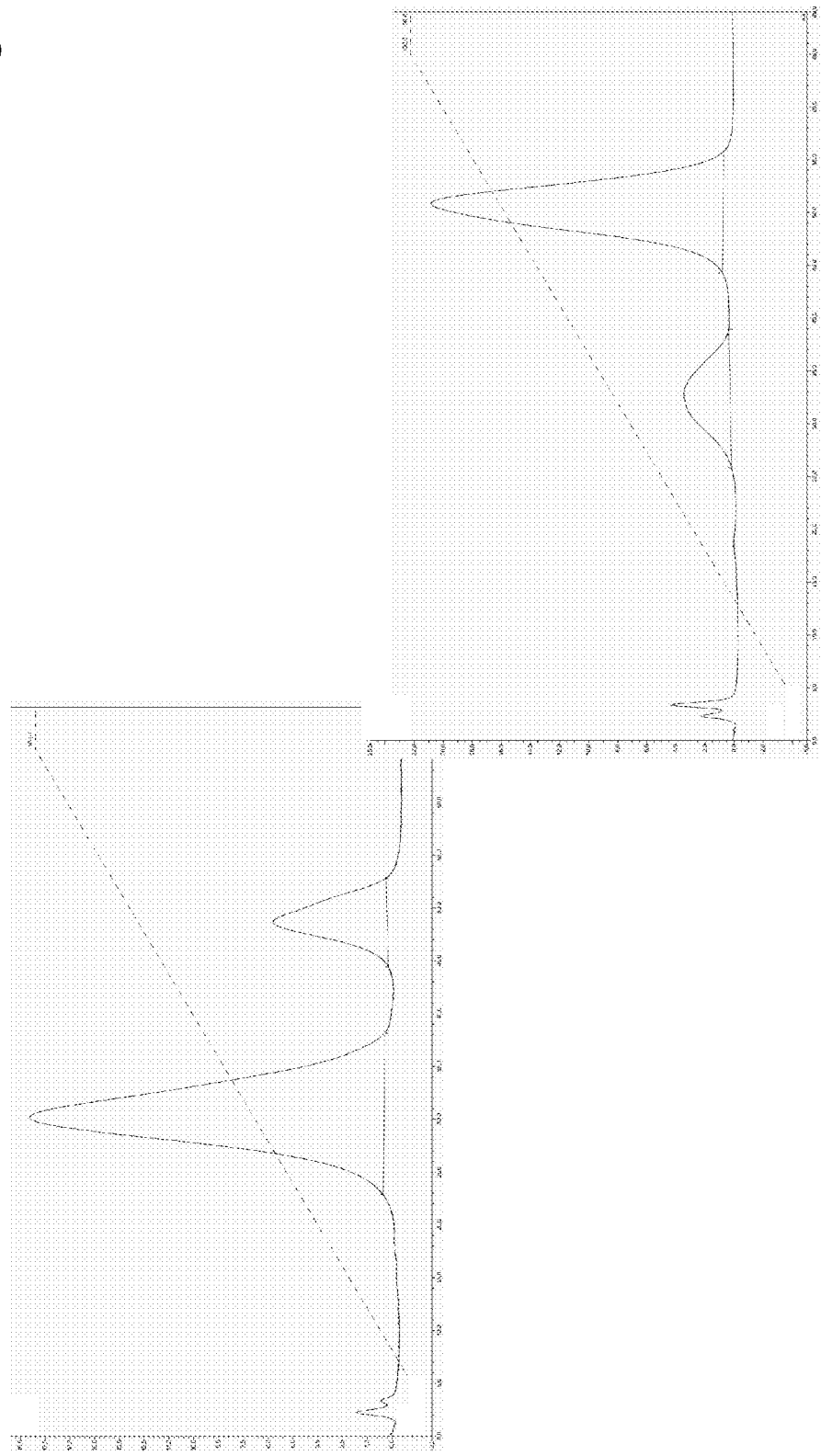
FIG. 4 Separation and quantification of different glycosylation forms of an anti-Her antibody (wild-type, at top) and a glycoengineered anti-Her antibody.

In FIG. 4 separation and quantification of different glycosylation forms of an anti-Her antibody (wild-type, at top) and a glycoengineered anti-Her antibody on a Fc-FcgRIIIa column is shown. Time of analysis could be shortened by modifying the gradient while retaining resolution.

Comparison of Affinity Column Using FcgammaRIIIaV158 and Fc Tagged FcgammaRIIIaV158

Figure 5:
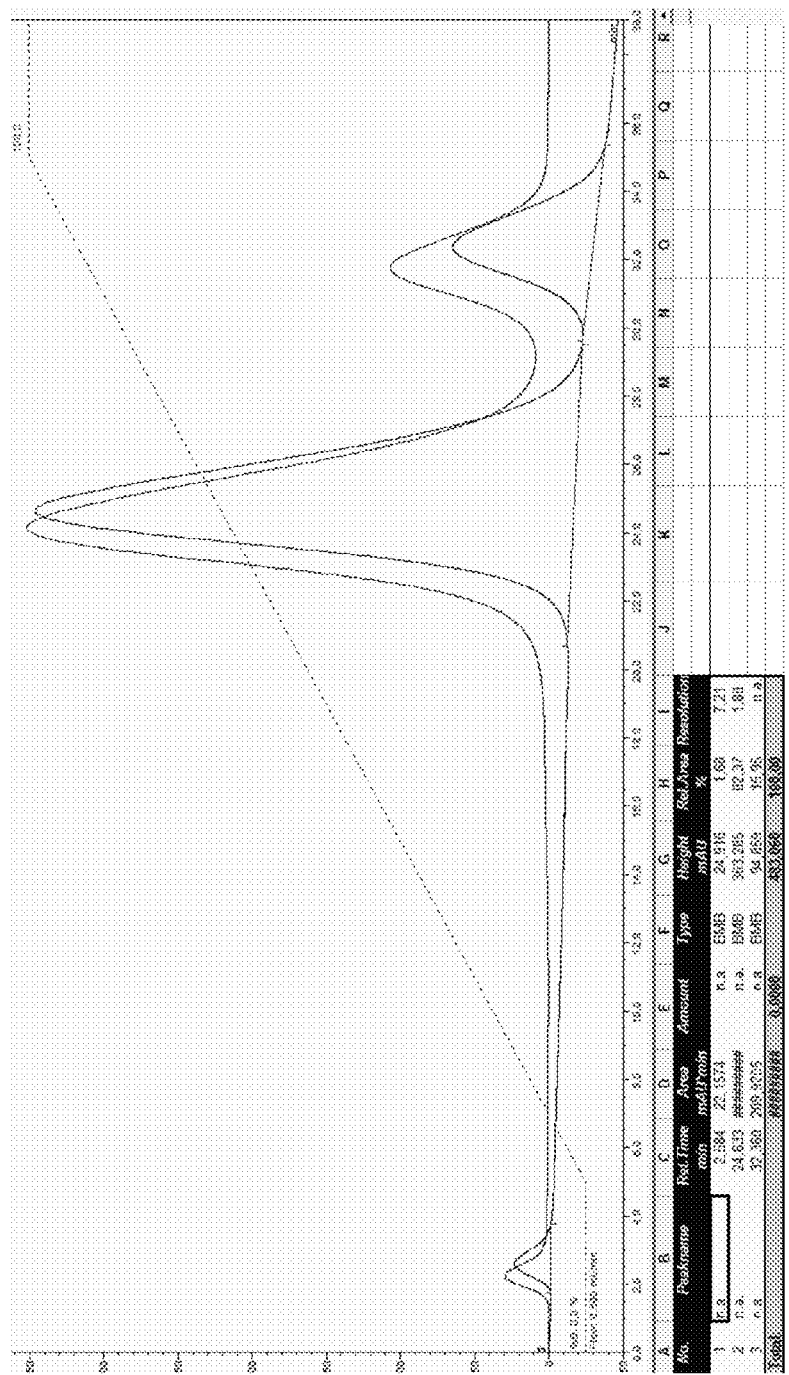
FIG. 5 Comparison of affinity column using FcgammaRIIIaV158 and Fc tagged FcgammaRIIIaV158.

After coupling both receptor constructs in equimolar amounts, the affinity columns behave equal in separating completely fucosylated and afucosylated antibodies (FIG. 5: black: FcgammaRIIIaV158; blue: FcgammaRIIIaV158-Fc).

Example 9

FcγRIIIaV158-Avi-IgA Protease-Fc LALA P329G-IgG Interaction Measurement

The BIAcore® system is well established for the study of molecule interactions. It allows a continuous real-time monitoring of ligand/analyte bindings and thus the determination of association rate constants ($k_a$), dissociation rate constants ($k_d$), and equilibrium constants ($K_D$). Changes in the refractive index indicate mass changes on the surface caused by the interaction of immobilized ligand with analyte injected in solution. If molecules bind immobilized ligands on the surface the mass increases, in case of dissociation the mass decreases.

For the activity determination of the FcgammaRIIaV158-Fc LALA P329G fusion polypeptide a direct binding assay was used.

Around 400 resonance units (RU) of the capturing system (20 μg/ml human Fab capture Kit GE Healthcare, 28-9583-25) were coupled onto a CM5 chip (GE Healthcare BR1005-30) at pH 5.0 using an amine coupling kit supplied by GE. The sample and system buffer was HBS-P+ pH 7.4 (10 mM HEPES, pH 7.4, 150 mM NaCl, 0.05% (v/v) Surfactant P20). The flow cell was set to 25° C. and sample block to 12° C. An antibody was captured by injecting a 50 nM solution for 360 sec. at a flow of 10 μl/min. Binding was measured by injection of 50 nM of FcgammaRIIIa fusion polypeptide for 180 sec. at a flow of 50 μl/min for association and 360 sec. for dissociation. The surface was regenerated by 60 sec. washing with glycine pH 2.1 solution at a flow rate of 20 μl/min. For the activity evaluation of the constructs the signal heights and dissociation behavior have been compared.

As shown in FIG. 6 the response of the FcgammaRIIaV158-Fc LALA P329G fusion polypeptide display more than 100 Response units in comparison to the FcgammaRIIaV158 with 40 RU.

Example 10

FcγRIIIaV158-Avi-IgA Protease-Fc LALA P329G Fusion Polypeptide IgG Kinetic Interaction Measurement Before and After Cleavage For the activity determination of the cleaved FcgammaRIIIaV158-Fc LALA P329G fusion polypeptide a direct binding assay was used. Around 400 resonance units (RU) of the capturing system (20 μg/ml human Fab capture Kit GE Healthcare, 28-9583-25) were coupled onto a CM5 chip (GE Healthcare BR1005-30) at pH 5.0 using an amine coupling kit supplied by GE. The sample and system buffer was HBS-P+ pH 7.4 (10 mM HEPES, pH 7.4, 150 mM NaCl, 0.05% (v/v) Surfactant P20). The flow cell was set to 25° C. and sample block to 12° C. An antibody was captured by injecting a 50 nM solution for 80 sec. at a flow of 10 μl/min.

Different concentrations of antibodies ranging from 0 to 250 nM (1:2 dilutions) were passed with a flow rate of 30 μl/min through the flow cells to measure the association at 25° C. for 120 sec. The dissociation phase was monitored for 420 sec. by switching from the sample solution to running buffer. The surface was regenerated by 60 sec. washing with glycine pH 2.1 solution at a flow rate of 20 μl/min.

Bulk refractive index differences were corrected for by subtracting the response obtained from a surface without captured FcγRIIIaV158. Blank Buffer injections are also subtracted (=double referencing).

Figure 7A:
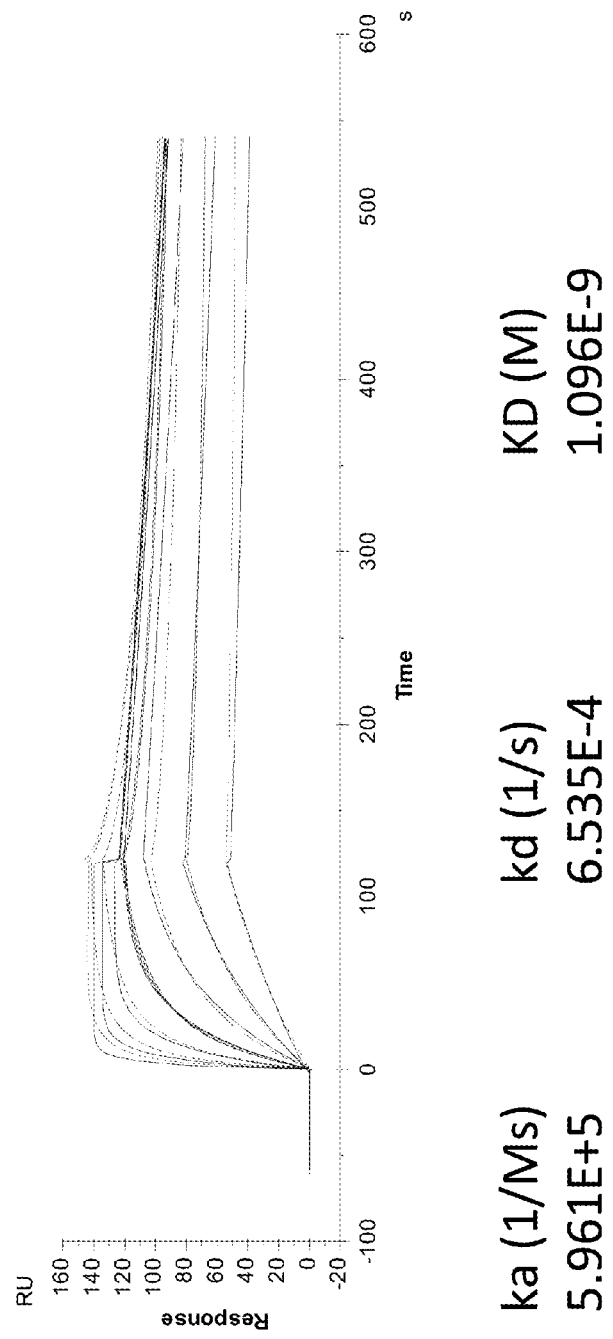
FIG. 7A Sensogram of Fcgamma receptor V158-Fc LALA P329G fusion polypeptide.
Figure 7B:
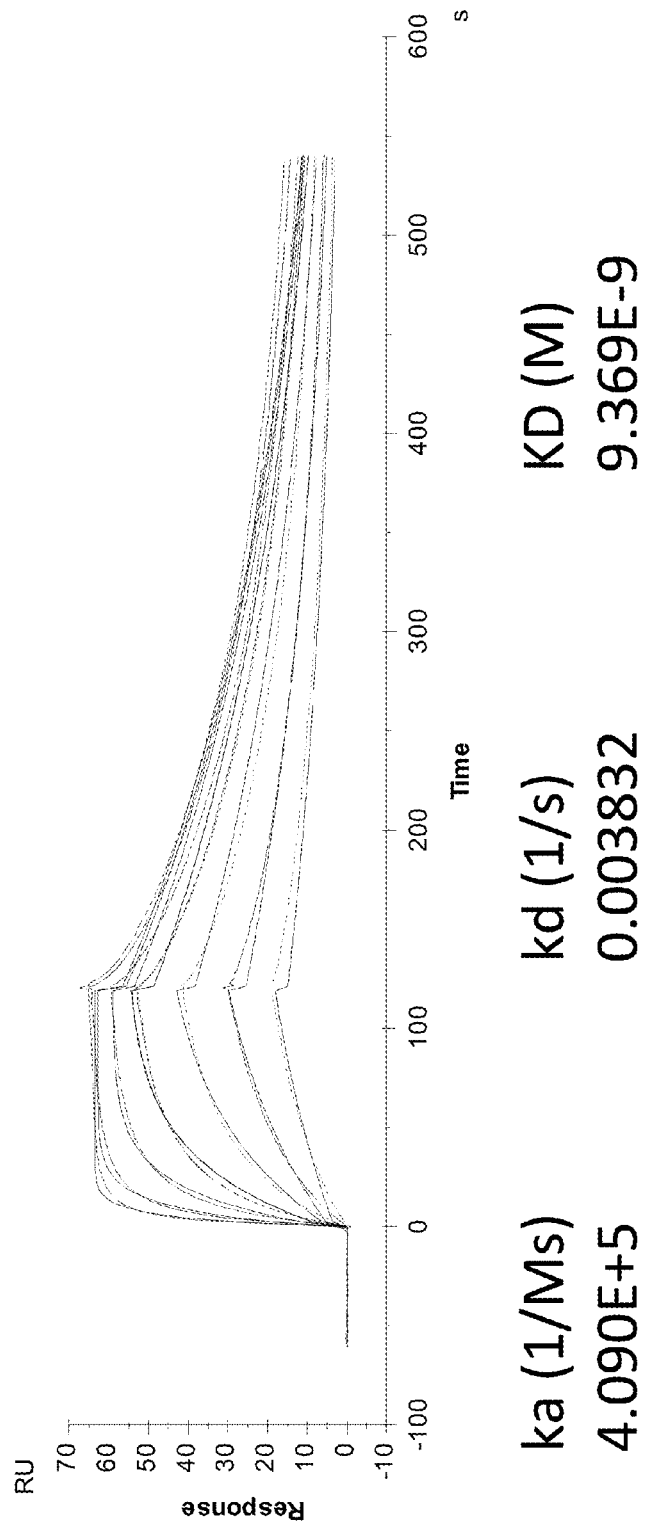
FIG. 7B Sensogram Fcgamma receptor V158.

The equilibrium dissociation constant ($K_D$), defined as $k_a/k_d$, was determined by analyzing the sensorgram curves obtained with several different concentrations, using BIAevaluation software package. The fitting of the data followed a suitable binding model. In FIG. 7 the sensograms of Fcgamma receptor V158-Fc LALA P329G fusion polypeptide (FIG. 7a), Fcgamma receptor V158 (FIG. 7b), cleaved Fcgamma receptor V158-Fc LALA P329G fusion polypeptide (FIG. 7c) is shown.

The invention claimed is:

1. A method for the production of a soluble Fc-receptor, said method comprising the following steps:
   a) cultivating in a cultivation medium a cell comprising a nucleic acid encoding a fusion polypeptide of formula I:

R1-FC-R2         (formula I)

wherein:
   R1 denotes a first Fc-receptor,
   R2 denotes a second Fc-receptor, and
   FC denotes a heavy chain Fc-region polypeptide,
   wherein R1 or R2 or both are present,
   wherein FC does not bind to R1 and/or R2,
   wherein FC is selected from human IgG1 heavy chain polypeptide comprising the amino acid sequence of SEQ ID NO: 1 with the mutations L234A, L235A and P329G, human IgG4 heavy chain polypeptide comprising the amino acid sequence of SEQ ID NO: 15 with the mutations S228P and L235E, and human IgG1 heavy chain polypeptide comprising the amino acid sequence of SEQ ID NO: 1 with the mutations 1253A, H310A, and H435A,
   b) recovering said fusion polypeptide from said cell or said cultivation medium, and
   c) optionally, cleaving said fusion polypeptide with a protease, thereby producing said soluble Fc-receptor.

2. The method of claim 1, wherein said fusion polypeptide has the formula II

R1-CS1-L1-CS2-FC-CS3-L2-CS4-R2         (formula II)

wherein:
   R1 denotes a first Fc-receptor,
   R2 denotes a second Fc-receptor,
   FC denotes a heavy chain Fc-region polypeptide,
   CS1 denotes a first cleavage site,
   CS2 denotes a second cleavage site,
   CS3 denotes a third cleavage site,
   CS4 denotes a fourth cleavage site,
   L1 denotes a first linker, and
   L2 denotes a second linker,
   wherein R1 or R2 or both are present,
   wherein any one of CS1, CS2, CS3, CS4 can independently of each other be present or absent,
   wherein L1 and L2 can independently of each other be present or absent, and
   wherein FC does not bind to R1 and/or R2.

3. The method of claim 1 or 2, wherein said soluble Fc receptor comprises two fusion polypeptides of Formula I or Formula II.

* * * * *

SEQUENCE LISTING

<160> NUMBER OF SEQ ID NOS: 60

<210> SEQ ID NO 1
<211> LENGTH: 107
<212> TYPE: PRT
<213> ORGANISM: Homo sapiens

<400> SEQUENCE: 1

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Trp Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Glu Ser Thr Tyr Arg Trp Ser Val Leu Thr Val Leu His Gln Asp Trp
65                  70                  75                  80

Leu Asn Gly Lys Glu Tyr Lys Cys Lys Val Ser Asn Lys Ala Leu Pro
                85                  90                  95

Ala Pro Ile Glu Lys Thr Ile Ser Lys Ala Lys
            100                 105

<210> SEQ ID NO 2
<211> LENGTH: 106
<212> TYPE: PRT
<213> ORGANISM: Homo sapiens

<400> SEQUENCE: 2

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 3
<211> LENGTH: 227
<212> TYPE: PRT
<213> ORGANISM: Homo sapiens

<400> SEQUENCE: 3

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 4
<211> LENGTH: 227
<212> TYPE: PRT
<213> ORGANISM: Artificial Sequence
<220> FEATURE:
<223> OTHER INFORMATION: variant human Fc-region of the IgG1 isotype
      with the mutations L234A, L235A

<400> SEQUENCE: 4

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val

```
                    180                 185                 190
Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 5
<211> LENGTH: 227
<212> TYPE: PRT
<213> ORGANISM: Artificial Sequence
<220> FEATURE:
<223> OTHER INFORMATION: variant human Fc-region of the IgG1 isotype
      with a hole mutation

<400> SEQUENCE: 5

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 6
<211> LENGTH: 227
<212> TYPE: PRT
<213> ORGANISM: Artificial Sequence
<220> FEATURE:
<223> OTHER INFORMATION: variant human Fc-region of the IgG1 isotype
      with a knob mutation

<400> SEQUENCE: 6

Asp Lys Thr His Thr Cys Pro Pro Cys Pro Ala Pro Glu Leu Leu Gly
```

```
1               5                   10                  15
Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
            130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 7
<211> LENGTH: 227
<212> TYPE: PRT
<213> ORGANISM: Artificial Sequence
<220> FEATURE:
<223> OTHER INFORMATION: variant human Fc-region of the IgG1 isotype
      with a L234A, L235A and hole mutation

<400> SEQUENCE: 7

Asp Lys Thr His Thr Cys Pro Pro Cys Pro Ala Pro Glu Ala Ala Gly
 1               5                  10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125
```

-continued

```
Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 8
<211> LENGTH: 227
<212> TYPE: PRT
<213> ORGANISM: Artificial Sequence
<220> FEATURE:
<223> OTHER INFORMATION: variant human Fc-region of the IgG1 isotype
      with a L234A, L235A and knob mutation

<400> SEQUENCE: 8

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 9
```

<211> LENGTH: 227
<212> TYPE: PRT
<213> ORGANISM: Artificial Sequence
<220> FEATURE:
<223> OTHER INFORMATION: variant human Fc-region of the IgG1 isotype
      with a P329G mutation

<400> SEQUENCE: 9

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 10
<211> LENGTH: 227
<212> TYPE: PRT
<213> ORGANISM: Artificial Sequence
<220> FEATURE:
<223> OTHER INFORMATION: variant human Fc-region of the IgG1 isotype
      with a L234A, L235A and P329G mutation

<400> SEQUENCE: 10

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

```
Arg Val Val Ser Val Leu Thr Val Leu His Gln Asp Trp Leu Asn Gly
            85                  90                  95

Lys Glu Tyr Lys Cys Lys Val Ser Asn Lys Ala Leu Gly Ala Pro Ile
        100                 105                 110

Glu Lys Thr Ile Ser Lys Ala Lys Gly Gln Pro Arg Glu Pro Gln Val
    115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 11
<211> LENGTH: 227
<212> TYPE: PRT
<213> ORGANISM: Artificial Sequence
<220> FEATURE:
<223> OTHER INFORMATION: variant human Fc-region of the IgG1 isotype
      with a P239G and hole mutation

<400> SEQUENCE: 11

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Gly Ala Pro Ile
        100                 105                 110

Glu Lys Thr Ile Ser Lys Ala Lys Gly Gln Pro Arg Glu Pro Gln Val
    115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
```

```
                195                 200                 205
His Glu Ala Leu His Asn His Tyr Thr Gln Lys Ser Leu Ser Leu Ser
    210                 215                 220

Pro Gly Lys
225

<210> SEQ ID NO 12
<211> LENGTH: 227
<212> TYPE: PRT
<213> ORGANISM: Artificial Sequence
<220> FEATURE:
<223> OTHER INFORMATION: variant human Fc-region of the IgG1 isotype
      with a P329G and knob mutation

<400> SEQUENCE: 12

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 13
<211> LENGTH: 227
<212> TYPE: PRT
<213> ORGANISM: Artificial Sequence
<220> FEATURE:
<223> OTHER INFORMATION: variant human Fc-region of the IgG1 isotype
      with a L234A, L235A, P329G and hole mutation

<400> SEQUENCE: 13

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
```

```
                20                  25                  30
Ile Ser Arg Thr Pro Glu Val Thr Cys Val Val Val Asp Val Ser His
         35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Gly Ala Pro Ile
            100                 105                 110
Glu Lys Thr Ile Ser Lys Ala Lys Gly Gln Pro Arg Glu Pro Gln Val
            115                 120                 125
Cys Thr Leu Pro Pro Ser Arg Asp Glu Leu Thr Lys Asn Gln Val Ser
        130                 135                 140
Leu Ser Cys Ala Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Val Ser Lys Leu Thr Val
            180                 185                 190
Asp Lys Ser Arg Trp Gln Gln Gly Asn Val Phe Ser Cys Ser Val Met
            195                 200                 205
His Glu Ala Leu His Asn His Tyr Thr Gln Lys Ser Leu Ser Leu Ser
        210                 215                 220
Pro Gly Lys
225

<210> SEQ ID NO 14
<211> LENGTH: 227
<212> TYPE: PRT
<213> ORGANISM: Artificial Sequence
<220> FEATURE:
<223> OTHER INFORMATION: variant human Fc-region of the IgG1 isotype
      with a L234A, L235A, P329G and knob mutation

<400> SEQUENCE: 14

Asp Lys Thr His Thr Cys Pro Pro Cys Pro Ala Pro Glu Ala Ala Gly
1               5                  10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
         35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Gly Ala Pro Ile
            100                 105                 110
Glu Lys Thr Ile Ser Lys Ala Lys Gly Gln Pro Arg Glu Pro Gln Val
            115                 120                 125
Tyr Thr Leu Pro Pro Cys Arg Asp Glu Leu Thr Lys Asn Gln Val Ser
        130                 135                 140
```

-continued

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 15
<211> LENGTH: 229
<212> TYPE: PRT
<213> ORGANISM: Homo sapiens

<400> SEQUENCE: 15

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 16
<211> LENGTH: 229
<212> TYPE: PRT
<213> ORGANISM: Artificial Sequence
<220> FEATURE:
<223> OTHER INFORMATION: variant human Fc-region of the IgG4 isotype
      with a S228P and L235E mutation

<400> SEQUENCE: 16

```
Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 17
<211> LENGTH: 229
<212> TYPE: PRT
<213> ORGANISM: Artificial Sequence
<220> FEATURE:
<223> OTHER INFORMATION: variant human Fc-region of the IgG4 isotype
       with a S228P, L235E and P329G mutation

<400> SEQUENCE: 17

```
Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110
```

```
Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225

<210> SEQ ID NO 18
<211> LENGTH: 191
<212> TYPE: PRT
<213> ORGANISM: Homo sapiens

<400> SEQUENCE: 18

Met Arg Thr Glu Asp Leu Pro Lys Ala Val Val Phe Leu Glu Pro Gln
1               5                   10                  15

Trp Tyr Arg Val Leu Glu Lys Asp Ser Val Thr Leu Lys Cys Gln Gly
            20                  25                  30

Ala Tyr Ser Pro Glu Asp Asn Ser Thr Gln Trp Phe His Asn Glu Ser
        35                  40                  45

Leu Ile Ser Ser Gln Ala Ser Ser Tyr Phe Ile Asp Ala Ala Thr Val
    50                  55                  60

Asp Asp Ser Gly Glu Tyr Arg Cys Gln Thr Asn Leu Ser Thr Leu Ser
65                  70                  75                  80

Asp Pro Val Gln Leu Glu Val His Ile Gly Trp Leu Leu Leu Gln Ala
                85                  90                  95

Pro Arg Trp Val Phe Lys Glu Glu Asp Pro Ile His Leu Arg Cys His
            100                 105                 110

Ser Trp Lys Asn Thr Ala Leu His Lys Val Thr Tyr Leu Gln Asn Gly
        115                 120                 125

Lys Gly Arg Lys Tyr Phe His His Asn Ser Asp Phe Tyr Ile Pro Lys
    130                 135                 140

Ala Thr Leu Lys Asp Ser Gly Ser Tyr Phe Cys Arg Gly Leu Val Gly
145                 150                 155                 160

Ser Lys Asn Val Ser Ser Glu Thr Val Asn Ile Thr Ile Thr Gln Gly
                165                 170                 175

Leu Ala Val Ser Thr Ile Ser Ser Phe Phe Pro Pro Gly Tyr Gln
            180                 185                 190

<210> SEQ ID NO 19
<211> LENGTH: 5
<212> TYPE: PRT
<213> ORGANISM: Artificial Sequence
<220> FEATURE:
<223> OTHER INFORMATION: Arg-tag

<400> SEQUENCE: 19
```

Arg Arg Arg Arg Arg
1               5

<210> SEQ ID NO 20
<211> LENGTH: 6
<212> TYPE: PRT
<213> ORGANISM: Artificial Sequence
<220> FEATURE:
<223> OTHER INFORMATION: Arg-tag 2

<400> SEQUENCE: 20

Arg Arg Arg Arg Arg Arg
1               5

<210> SEQ ID NO 21
<211> LENGTH: 15
<212> TYPE: PRT
<213> ORGANISM: Artificial Sequence
<220> FEATURE:
<223> OTHER INFORMATION: Avi-tag

<400> SEQUENCE: 21

Gly Leu Asn Asp Ile Phe Glu Ala Gln Lys Ile Glu Trp His Glu
1               5                   10                  15

<210> SEQ ID NO 22
<211> LENGTH: 21
<212> TYPE: PRT
<213> ORGANISM: Artificial Sequence
<220> FEATURE:
<223> OTHER INFORMATION: His-Avi-tag

<400> SEQUENCE: 22

His His His His His His Gly Leu Asn Asp Ile Phe Glu Ala Gln Lys
1               5                   10                  15

Ile Glu Trp His Glu
            20

<210> SEQ ID NO 23
<211> LENGTH: 6
<212> TYPE: PRT
<213> ORGANISM: Artificial Sequence
<220> FEATURE:
<223> OTHER INFORMATION: His-tag

<400> SEQUENCE: 23

His His His His His His
1               5

<210> SEQ ID NO 24
<211> LENGTH: 19
<212> TYPE: PRT
<213> ORGANISM: Artificial Sequence
<220> FEATURE:
<223> OTHER INFORMATION: amino acid tag

<400> SEQUENCE: 24

Lys Asp His Leu Ile His Asn Val His Lys Glu Phe His Ala His Ala
1               5                   10                  15

His Asn Lys

<210> SEQ ID NO 25
<211> LENGTH: 8
<212> TYPE: PRT
<213> ORGANISM: Artificial Sequence
<220> FEATURE:

<223> OTHER INFORMATION: amino acid tag

<400> SEQUENCE: 25

Asp Tyr Lys Asp Asp Asp Asp Lys
1               5

<210> SEQ ID NO 26
<211> LENGTH: 22
<212> TYPE: PRT
<213> ORGANISM: Artificial Sequence
<220> FEATURE:
<223> OTHER INFORMATION: amino acid tag

<400> SEQUENCE: 26

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 27
<211> LENGTH: 9
<212> TYPE: PRT
<213> ORGANISM: Artificial Sequence
<220> FEATURE:
<223> OTHER INFORMATION: amino acid tag#

<400> SEQUENCE: 27

Ala Trp Arg His Pro Gln Phe Gly Gly
1               5

<210> SEQ ID NO 28
<211> LENGTH: 8
<212> TYPE: PRT
<213> ORGANISM: Artificial Sequence
<220> FEATURE:
<223> OTHER INFORMATION: amino acid tag

<400> SEQUENCE: 28

Trp Ser His Pro Gln Phe Glu Lys
1               5

<210> SEQ ID NO 29
<211> LENGTH: 10
<212> TYPE: PRT
<213> ORGANISM: Artificial Sequence
<220> FEATURE:
<223> OTHER INFORMATION: amino acid tag

<400> SEQUENCE: 29

Met Asp Val Glu Ala Trp Leu Gly Ala Arg
1               5                   10

<210> SEQ ID NO 30
<211> LENGTH: 16
<212> TYPE: PRT
<213> ORGANISM: Artificial Sequence
<220> FEATURE:
<223> OTHER INFORMATION: amino acid tag

<400> SEQUENCE: 30

Met Asp Val Glu Ala Trp Leu Gly Ala Arg Val Pro Leu Val Glu Thr
1               5                   10                  15

<210> SEQ ID NO 31
<211> LENGTH: 38
<212> TYPE: PRT

<213> ORGANISM: Artificial Sequence
<220> FEATURE:
<223> OTHER INFORMATION: amino acid tag

<400> SEQUENCE: 31

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 32
<211> LENGTH: 10
<212> TYPE: PRT
<213> ORGANISM: Artificial Sequence
<220> FEATURE:
<223> OTHER INFORMATION: amino acid tag

<400> SEQUENCE: 32

Glu Gln Lys Leu Ile Ser Glu Glu Asp Leu
1               5                   10

<210> SEQ ID NO 33
<211> LENGTH: 15
<212> TYPE: PRT
<213> ORGANISM: Artificial Sequence
<220> FEATURE:
<223> OTHER INFORMATION: amino acid tag

<400> SEQUENCE: 33

Lys Glu Thr Ala Ala Ala Lys Phe Glu Arg Gln His Met Asp Ser
1               5                   10                  15

<210> SEQ ID NO 34
<211> LENGTH: 26
<212> TYPE: PRT
<213> ORGANISM: Artificial Sequence
<220> FEATURE:
<223> OTHER INFORMATION: amino acid tag

<400> SEQUENCE: 34

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 35
<211> LENGTH: 47
<212> TYPE: PRT
<213> ORGANISM: Artificial Sequence
<220> FEATURE:
<223> OTHER INFORMATION: amino acid tag

<400> SEQUENCE: 35

Pro Ala Thr Thr Thr Gly Ser Ser Pro Gly Pro Thr Gln Ser His Tyr
1               5                   10                  15

Gly Gln Cys Gly Gly Ile Gly Tyr Ser Gly Pro Thr Val Cys Ala Ser
            20                  25                  30

Gly Thr Thr Cys Gln Val Leu Asn Pro Tyr Tyr Ser Gln Cys Leu
        35                  40                  45

<210> SEQ ID NO 36
<211> LENGTH: 32

```
<212> TYPE: PRT
<213> ORGANISM: Butyrivibrio fibrisolvens

<400> SEQUENCE: 36

Met Asp Trp Asn Ala Asn Ile Ala Pro Gly Asn Ser Val Glu Phe Gly
1               5                   10                  15

Ile Gln Gly Ala Gly Ser Val Gly Asn Val Ile Asp Ile Thr Val Glu
            20                  25                  30

<210> SEQ ID NO 37
<211> LENGTH: 51
<212> TYPE: PRT
<213> ORGANISM: Artificial Sequence
<220> FEATURE:
<223> OTHER INFORMATION: chitin-binding-domain

<400> SEQUENCE: 37

Thr Asn Pro Gly Val Ser Ala Trp Gln Val Asn Thr Ala Tyr Thr Ala
1               5                   10                  15

Gly Gln Leu Val Thr Tyr Asn Gly Lys Thr Tyr Lys Cys Leu Gln Pro
            20                  25                  30

His Thr Ser Leu Ala Gly Trp Glu Pro Ser Asn Val Pro Ala Leu Trp
        35                  40                  45

Gln Leu Gln
    50

<210> SEQ ID NO 38
<211> LENGTH: 209
<212> TYPE: PRT
<213> ORGANISM: Chondrus crispus

<400> SEQUENCE: 38

Met Pro Glu Ile Lys Leu Thr Tyr Phe Asp Met Arg Gly Arg Ala Glu
1               5                   10                  15

Ala Ser Arg Leu Ala Leu Val Val Gly Glu Ile Pro Phe Glu Asp Glu
            20                  25                  30

Arg Val Val Phe Asp His Trp Lys Glu Ala Lys Pro Lys Thr Pro Tyr
        35                  40                  45

Ala Ala Leu Pro Met Leu Thr Val Asp Gly Met Gln Val Ala Gln Ser
    50                  55                  60

Asp Ala Ile Leu Arg Tyr Cys Gly Lys Leu Ala Gly Leu Tyr Pro Ser
65                  70                  75                  80

Asp Pro Leu Glu Ala Ala Lys Val Asp Glu Val Gly Val Ile Asp
                85                  90                  95

Asp Val Thr His Ala Met Tyr Arg Tyr Arg Gly Asp Asp Lys Asp Lys
                100                 105                 110

Leu Arg Glu Glu Arg Asp Lys Phe Ser Lys Val Asp Val Pro Arg Tyr
            115                 120                 125

Val Gly Ala Leu Glu Lys Arg Leu Glu Ala Phe Gly Asp Gly Pro Trp
        130                 135                 140

Ala Val Gly Gly Asn Met Thr Ile Ala Asp Leu His Ile Cys His Leu
145                 150                 155                 160

Val Thr Asn Ile Arg Cys Gly Met Leu Asp Phe Val Asp Lys Asp Leu
                165                 170                 175

Leu Glu Gly Tyr Val Arg Ile Val Lys Ser Tyr Ser Ala Val Met Glu
            180                 185                 190

His Pro Lys Val Thr Glu Trp Tyr Glu Lys Lys Pro Val Lys Met Phe
        195                 200                 205
```

Ser

<210> SEQ ID NO 39
<211> LENGTH: 396
<212> TYPE: PRT
<213> ORGANISM: Escherichia coli

<400> SEQUENCE: 39

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365
```

```
Val Arg Thr Ala Val Ile Asn Ala Ala Ser Gly Arg Gln Thr Val Asp
    370                 375                 380

Glu Ala Leu Lys Asp Ala Gln Thr Arg Ile Thr Lys
385                 390                 395

<210> SEQ ID NO 40
<211> LENGTH: 5
<212> TYPE: PRT
<213> ORGANISM: Artificial Sequence
<220> FEATURE:
<223> OTHER INFORMATION: protease cleavage site

<400> SEQUENCE: 40

Pro Ala Pro Ser Pro
1               5

<210> SEQ ID NO 41
<211> LENGTH: 4
<212> TYPE: PRT
<213> ORGANISM: Artificial Sequence
<220> FEATURE:
<223> OTHER INFORMATION: protease cleavage site

<400> SEQUENCE: 41

Pro Pro Ser Pro
1

<210> SEQ ID NO 42
<211> LENGTH: 4
<212> TYPE: PRT
<213> ORGANISM: Artificial Sequence
<220> FEATURE:
<223> OTHER INFORMATION: protease cleavage site

<400> SEQUENCE: 42

Pro Pro Ala Pro
1

<210> SEQ ID NO 43
<211> LENGTH: 4
<212> TYPE: PRT
<213> ORGANISM: Artificial Sequence
<220> FEATURE:
<223> OTHER INFORMATION: protease cleavage site

<400> SEQUENCE: 43

Pro Pro Thr Pro
1

<210> SEQ ID NO 44
<211> LENGTH: 4
<212> TYPE: PRT
<213> ORGANISM: Artificial Sequence
<220> FEATURE:
<223> OTHER INFORMATION: protease cleavage site

<400> SEQUENCE: 44

Pro Pro Gly Pro
1

<210> SEQ ID NO 45
<211> LENGTH: 6
<212> TYPE: PRT
<213> ORGANISM: Artificial Sequence
<220> FEATURE:
<223> OTHER INFORMATION: enzymatic cleavage site
```

```
<400> SEQUENCE: 45

Pro Arg Pro Pro Thr Pro
1               5

<210> SEQ ID NO 46
<211> LENGTH: 7
<212> TYPE: PRT
<213> ORGANISM: Artificial Sequence
<220> FEATURE:
<223> OTHER INFORMATION: enzymatic cleavage site

<400> SEQUENCE: 46

Val Val Ala Pro Pro Ala Pro
1               5

<210> SEQ ID NO 47
<211> LENGTH: 7
<212> TYPE: PRT
<213> ORGANISM: Artificial Sequence
<220> FEATURE:
<223> OTHER INFORMATION: enzymatic cleavage site

<400> SEQUENCE: 47

Val Val Ala Pro Pro Ser Pro
1               5

<210> SEQ ID NO 48
<211> LENGTH: 7
<212> TYPE: PRT
<213> ORGANISM: Artificial Sequence
<220> FEATURE:
<223> OTHER INFORMATION: enzymatic cleavage site

<400> SEQUENCE: 48

Val Val Ala Pro Pro Thr Pro
1               5

<210> SEQ ID NO 49
<211> LENGTH: 7
<212> TYPE: PRT
<213> ORGANISM: Artificial Sequence
<220> FEATURE:
<223> OTHER INFORMATION: enzymatic cleavage site

<400> SEQUENCE: 49

Val Val Ala Pro Pro Gly Pro
1               5

<210> SEQ ID NO 50
<211> LENGTH: 6
<212> TYPE: PRT
<213> ORGANISM: Artificial Sequence
<220> FEATURE:
<223> OTHER INFORMATION: enzymatic cleavage site

<400> SEQUENCE: 50

Pro Arg Pro Pro Thr Pro
1               5

<210> SEQ ID NO 51
<211> LENGTH: 6
<212> TYPE: PRT
<213> ORGANISM: Artificial Sequence
<220> FEATURE:
<223> OTHER INFORMATION: enzymatic cleavage site
```

-continued

```
<400> SEQUENCE: 51

Ala Pro Pro Ala Ala Pro
1               5

<210> SEQ ID NO 52
<211> LENGTH: 6
<212> TYPE: PRT
<213> ORGANISM: Artificial Sequence
<220> FEATURE:
<223> OTHER INFORMATION: enzymatic cleavage site

<400> SEQUENCE: 52

Pro Arg Pro Pro Ala Pro
1               5

<210> SEQ ID NO 53
<211> LENGTH: 6
<212> TYPE: PRT
<213> ORGANISM: Artificial Sequence
<220> FEATURE:
<223> OTHER INFORMATION: enzymatic cleavage site

<400> SEQUENCE: 53

Pro Arg Pro Pro Ser Pro
1               5

<210> SEQ ID NO 54
<211> LENGTH: 6
<212> TYPE: PRT
<213> ORGANISM: Artificial Sequence
<220> FEATURE:
<223> OTHER INFORMATION: enzymatic cleavage site

<400> SEQUENCE: 54

Pro Arg Pro Pro Gly Pro
1               5

<210> SEQ ID NO 55
<211> LENGTH: 19
<212> TYPE: PRT
<213> ORGANISM: Mus musculus

<400> SEQUENCE: 55

Met Gly Trp Ser Cys Ile Ile Leu Phe Leu Val Ala Thr Ala Thr Gly
1               5                   10                  15

Val His Ser

<210> SEQ ID NO 56
<211> LENGTH: 443
<212> TYPE: PRT
<213> ORGANISM: Artificial Sequence
<220> FEATURE:
<223> OTHER INFORMATION: mature FcyRIIIaV158-Avi-IgA Protease-Fc LALA
      P239G fusion polypeptide

<400> SEQUENCE: 56

Gly Met Arg Thr Glu Asp Leu Pro Lys Ala Val Val Phe Leu Glu Pro
1               5                   10                  15

Gln Trp Tyr Arg Val Leu Glu Lys Asp Ser Val Thr Leu Lys Cys Gln
                20                  25                  30

Gly Ala Tyr Ser Pro Glu Asp Asn Ser Thr Gln Trp Phe His Asn Glu
            35                  40                  45

Ser Leu Ile Ser Ser Gln Ala Ser Ser Tyr Phe Ile Asp Ala Ala Thr
        50                  55                  60
```

Val Asp Asp Ser Gly Glu Tyr Arg Cys Gln Thr Asn Leu Ser Thr Leu
65                  70                  75                  80

Ser Asp Pro Val Gln Leu Glu Val His Ile Gly Trp Leu Leu Leu Gln
            85                  90                  95

Ala Pro Arg Trp Val Phe Lys Glu Glu Asp Pro Ile His Leu Arg Cys
        100                 105                 110

His Ser Trp Lys Asn Thr Ala Leu His Lys Val Thr Tyr Leu Gln Asn
    115                 120                 125

Gly Lys Gly Arg Lys Tyr Phe His His Asn Ser Asp Phe Tyr Ile Pro
130                 135                 140

Lys Ala Thr Leu Lys Asp Ser Gly Ser Tyr Phe Cys Arg Gly Leu Val
145                 150                 155                 160

Gly Ser Lys Asn Val Ser Ser Glu Thr Val Asn Ile Thr Ile Thr Gln
                165                 170                 175

Gly Leu Ala Val Ser Thr Ile Ser Ser Phe Phe Pro Pro Gly Tyr Gln
            180                 185                 190

Gly Leu Asn Asp Ile Phe Glu Ala Gln Lys Ile Glu Trp His Glu Leu
        195                 200                 205

Val Val Ala Pro Pro Ala Pro Glu Asp Lys Thr His Thr Cys Pro Pro
210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Ala Leu Gly Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 57
<211> LENGTH: 436
<212> TYPE: PRT
<213> ORGANISM: Artificial Sequence
<220> FEATURE:

<223> OTHER INFORMATION: FcyRIIa-LR(H131)-Avi-IgA Protease-Fc LALA P239G fusion polypeptide

<400> SEQUENCE: 57

| | | | | | | | | | | | | | | |
|---|---|---|---|---|---|---|---|---|---|---|---|---|---|---|
| Gln | Ala | Ala | Ala | Pro | Lys | Ala | Val | Leu | Lys | Leu | Glu | Pro | Pro | Trp |
| 1 | | | | 5 | | | | | 10 | | | | | 15 |
| Ile | Asn | Val | Leu | Gln | Glu | Asp | Ser | Val | Thr | Leu | Thr | Cys | Gln | Gly |  Ala |
| | | | 20 | | | | | 25 | | | | | 30 | |
| Arg | Ser | Pro | Glu | Ser | Asp | Ser | Ile | Gln | Trp | Phe | His | Asn | Gly | Asn | Leu |
| | | 35 | | | | | 40 | | | | | 45 | | |
| Ile | Pro | Thr | His | Thr | Gln | Pro | Ser | Tyr | Arg | Phe | Lys | Ala | Asn | Asn | Asn |
| | 50 | | | | | 55 | | | | | 60 | | | |
| Asp | Ser | Gly | Glu | Tyr | Thr | Cys | Gln | Thr | Gly | Gln | Thr | Ser | Leu | Ser | Asp |
| 65 | | | | | 70 | | | | | 75 | | | | | 80 |
| Pro | Val | His | Leu | Thr | Val | Leu | Ser | Glu | Trp | Leu | Val | Leu | Gln | Thr | Pro |
| | | | | 85 | | | | | 90 | | | | | 95 | |
| His | Leu | Glu | Phe | Gln | Glu | Gly | Glu | Thr | Ile | Met | Leu | Arg | Cys | His | Ser |
| | | | 100 | | | | | 105 | | | | | 110 | | |
| Trp | Lys | Asp | Lys | Pro | Leu | Val | Lys | Val | Thr | Phe | Phe | Gln | Asn | Gly | Lys |
| | | 115 | | | | | 120 | | | | | 125 | | | |
| Ser | Gln | Lys | Phe | Ser | His | Leu | Asp | Pro | Thr | Phe | Ser | Ile | Pro | Gln | Ala |
| | 130 | | | | | 135 | | | | | 140 | | | | |
| Asn | His | Ser | His | Ser | Gly | Asp | Tyr | His | Cys | Thr | Gly | Asn | Ile | Gly | Tyr |
| 145 | | | | | 150 | | | | | 155 | | | | | 160 |
| Thr | Leu | Phe | Ser | Ser | Lys | Pro | Val | Thr | Ile | Thr | Val | Gln | Val | Pro | Ser |
| | | | | 165 | | | | | 170 | | | | | 175 | |
| Met | Gly | Ser | Ser | Ser | Pro | Met | Gly | Ile | Gly | Leu | Asn | Asp | Ile | Phe | Glu |
| | | | 180 | | | | | 185 | | | | | 190 | | |
| Ala | Gln | Lys | Ile | Glu | Trp | His | Glu | Leu | Val | Val | Ala | Pro | Pro | Ala | Pro |
| | | 195 | | | | | 200 | | | | | 205 | | | |
| Glu | Asp | Lys | Thr | His | Thr | Cys | Pro | Pro | Cys | Pro | Ala | Pro | Glu | Ala | Ala |
| | 210 | | | | | 215 | | | | | 220 | | | | |
| Gly | Gly | Pro | Ser | Val | Phe | Leu | Phe | Pro | Pro | Lys | Pro | Lys | Asp | Thr | Leu |
| 225 | | | | | 230 | | | | | 235 | | | | | 240 |
| Met | Ile | Ser | Arg | Thr | Pro | Glu | Val | Thr | Cys | Val | Val | Val | Asp | Val | Ser |
| | | | | 245 | | | | | 250 | | | | | 255 | |
| His | Glu | Asp | Pro | Glu | Val | Lys | Phe | Asn | Trp | Tyr | Val | Asp | Gly | Val | Glu |
| | | | 260 | | | | | 265 | | | | | 270 | | |
| Val | His | Asn | Ala | Lys | Thr | Lys | Pro | Arg | Glu | Glu | Gln | Tyr | Asn | Ser | Thr |
| | | 275 | | | | | 280 | | | | | 285 | | | |
| Tyr | Arg | Val | Val | Ser | Val | Leu | Thr | Val | Leu | His | Gln | Asp | Trp | Leu | Asn |
| | 290 | | | | | 295 | | | | | 300 | | | | |
| Gly | Lys | Glu | Tyr | Lys | Cys | Lys | Val | Ser | Asn | Lys | Ala | Leu | Gly | Ala | Pro |
| 305 | | | | | 310 | | | | | 315 | | | | | 320 |
| Ile | Glu | Lys | Thr | Ile | Ser | Lys | Ala | Lys | Gly | Gln | Pro | Arg | Glu | Pro | Gln |
| | | | | 325 | | | | | 330 | | | | | 335 | |
| Val | Tyr | Thr | Leu | Pro | Pro | Ser | Arg | Asp | Glu | Leu | Thr | Lys | Asn | Gln | Val |
| | | | 340 | | | | | 345 | | | | | 350 | | |
| Ser | Leu | Thr | Cys | Leu | Val | Lys | Gly | Phe | Tyr | Pro | Ser | Asp | Ile | Ala | Val |
| | | 355 | | | | | 360 | | | | | 365 | | | |
| Glu | Trp | Glu | Ser | Asn | Gly | Gln | Pro | Glu | Asn | Asn | Tyr | Lys | Thr | Thr | Pro |
| | 370 | | | | | 375 | | | | | 380 | | | | |
| Pro | Val | Leu | Asp | Ser | Asp | Gly | Ser | Phe | Phe | Leu | Tyr | Ser | Lys | Leu | Thr |
| 385 | | | | | 390 | | | | | 395 | | | | | 400 |

Val Asp Lys Ser Arg Trp Gln Gln Gly Asn Val Phe Ser Cys Ser Val
            405                 410                 415

Met His Glu Ala Leu His Asn His Tyr Thr Gln Lys Ser Leu Ser Leu
            420                 425                 430

Ser Pro Gly Lys
        435

<210> SEQ ID NO 58
<211> LENGTH: 423
<212> TYPE: PRT
<213> ORGANISM: Artificial Sequence
<220> FEATURE:
<223> OTHER INFORMATION: FcγRIIb-Avi-IgA Protease-Fc LALA P239G fusion
      polypeptide

<400> SEQUENCE: 58

Ala Pro Pro Lys Ala Val Leu Lys Leu Glu Pro Gln Trp Ile Asn Val
1               5                   10                  15

Leu Gln Glu Asp Ser Val Thr Leu Thr Cys Arg Gly Thr His Ser Pro
            20                  25                  30

Glu Ser Asp Ser Ile Gln Trp Phe His Asn Gly Asn Leu Ile Pro Thr
        35                  40                  45

His Thr Gln Pro Ser Tyr Arg Phe Lys Ala Asn Asn Asn Asp Ser Gly
    50                  55                  60

Glu Tyr Thr Cys Gln Thr Gly Gln Thr Ser Leu Ser Asp Pro Val His
65                  70                  75                  80

Leu Thr Val Leu Ser Glu Trp Leu Val Leu Gln Thr Pro His Leu Glu
                85                  90                  95

Phe Gln Glu Gly Glu Thr Ile Val Leu Arg Cys His Ser Trp Lys Asp
            100                 105                 110

Lys Pro Leu Val Lys Val Thr Phe Phe Gln Asn Gly Lys Ser Lys Lys
        115                 120                 125

Phe Ser Arg Ser Asp Pro Asn Phe Ser Ile Pro Gln Ala Asn His Ser
    130                 135                 140

His Ser Gly Asp Tyr His Cys Thr Gly Asn Ile Gly Tyr Thr Leu Tyr
145                 150                 155                 160

Ser Ser Lys Pro Val Thr Ile Thr Val Gln Ala Pro Gly Leu Asn Asp
                165                 170                 175

Ile Phe Glu Ala Gln Lys Ile Glu Trp His Glu Leu Val Val Ala Pro
            180                 185                 190

Pro Ala Pro Glu Asp Lys Thr His Thr Cys Pro Pro Cys Pro Ala Pro
        195                 200                 205

Glu Ala Ala Gly Gly Pro Ser Val Phe Leu Phe Pro Pro Lys Pro Lys
    210                 215                 220

Asp Thr Leu Met Ile Ser Arg Thr Pro Glu Val Thr Cys Val Val Val
225                 230                 235                 240

Asp Val Ser His Glu Asp Pro Glu Val Lys Phe Asn Trp Tyr Val Asp
                245                 250                 255

Gly Val Glu Val His Asn Ala Lys Thr Lys Pro Arg Glu Glu Gln Tyr
            260                 265                 270

Asn Ser Thr Tyr Arg Val Val Ser Val Leu Thr Val Leu His Gln Asp
        275                 280                 285

Trp Leu Asn Gly Lys Glu Tyr Lys Cys Lys Val Ser Asn Lys Ala Leu
    290                 295                 300

Gly Ala Pro Ile Glu Lys Thr Ile Ser Lys Ala Lys Gly Gln Pro Arg

```
                    305                 310                 315                 320

Glu Pro Gln Val Tyr Thr Leu Pro Pro Ser Arg Asp Glu Leu Thr Lys
                325                 330                 335

Asn Gln Val Ser Leu Thr Cys Leu Val Lys Gly Phe Tyr Pro Ser Asp
            340                 345                 350

Ile Ala Val Glu Trp Glu Ser Asn Gly Gln Pro Glu Asn Asn Tyr Lys
        355                 360                 365

Thr Thr Pro Pro Val Leu Asp Ser Asp Gly Ser Phe Phe Leu Tyr Ser
    370                 375                 380

Lys Leu Thr Val Asp Lys Ser Arg Trp Gln Gln Gly Asn Val Phe Ser
385                 390                 395                 400

Cys Ser Val Met His Glu Ala Leu His Asn His Tyr Thr Gln Lys Ser
                405                 410                 415

Leu Ser Leu Ser Pro Gly Lys
            420

<210> SEQ ID NO 59
<211> LENGTH: 443
<212> TYPE: PRT
<213> ORGANISM: Artificial Sequence
<220> FEATURE:
<223> OTHER INFORMATION: FcyRIIIb-Avi-IgA Protease-Fc LALA P239G fusion
      polypeptide

<400> SEQUENCE: 59

Gly Met Arg Thr Glu Asp Leu Pro Lys Ala Val Val Phe Leu Glu Pro
1               5                   10                  15

Gln Trp Tyr Ser Val Leu Glu Lys Asp Ser Val Thr Leu Lys Cys Gln
            20                  25                  30

Gly Ala Tyr Ser Pro Glu Asp Asn Ser Thr Gln Trp Phe His Asn Glu
        35                  40                  45

Ser Leu Ile Ser Ser Gln Ala Ser Ser Tyr Phe Ile Asp Ala Ala Thr
    50                  55                  60

Val Asn Asp Ser Gly Glu Tyr Arg Cys Gln Thr Asn Leu Ser Thr Leu
65                  70                  75                  80

Ser Asp Pro Val Gln Leu Glu Val His Ile Gly Trp Leu Leu Leu Gln
                85                  90                  95

Ala Pro Arg Trp Val Phe Lys Glu Glu Asp Pro Ile His Leu Arg Cys
            100                 105                 110

His Ser Trp Lys Asn Thr Ala Leu His Lys Val Thr Tyr Leu Gln Asn
        115                 120                 125

Gly Lys Asp Arg Lys Tyr Phe His His Asn Ser Asp Phe His Ile Pro
    130                 135                 140

Lys Ala Thr Leu Lys Asp Ser Gly Ser Tyr Phe Cys Arg Gly Leu Val
145                 150                 155                 160

Gly Ser Lys Asn Val Ser Ser Glu Thr Val Asn Ile Thr Ile Thr Gln
                165                 170                 175

Gly Leu Ala Val Ser Thr Ile Ser Ser Phe Ser Pro Gly Tyr Gln
            180                 185                 190

Gly Leu Asn Asp Ile Phe Glu Ala Gln Lys Ile Glu Trp His Glu Leu
        195                 200                 205

Val Val Ala Pro Pro Ala Pro Glu Asp Lys Thr His Thr Cys Pro Pro
    210                 215                 220

Cys Pro Ala Pro Glu Ala Ala Gly Gly Pro Ser Val Phe Leu Phe Pro
225                 230                 235                 240
```

```
Pro Lys Pro Lys Asp Thr Leu Met Ile Ser Arg Thr Pro Glu Val Thr
            245                 250                 255

Cys Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
            275                 280                 285

Glu Glu Gln Tyr Asn Ser Thr Tyr Arg Val Val Ser Val Leu Thr Val
            290                 295                 300

Leu His Gln Asp Trp Leu Asn Gly Lys Glu Tyr Lys Cys Lys Val Ser
305                 310                 315                 320

Asn Lys Ala Leu Gly Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
            435                 440

<210> SEQ ID NO 60
<211> LENGTH: 346
<212> TYPE: PRT
<213> ORGANISM: Artificial Sequence
<220> FEATURE:
<223> OTHER INFORMATION: minimal FcyRIIIa-Avi-Fc LALA p239G fusion
      polypeptide

<400> SEQUENCE: 60

Gly Trp Leu Leu Leu Gln Ala Pro Arg Trp Val Phe Lys Glu Glu Asp
1               5                   10                  15

Pro Ile His Leu Arg Cys His Ser Trp Lys Asn Thr Ala Leu His Lys
            20                  25                  30

Val Thr Tyr Leu Gln Asn Gly Lys Gly Arg Lys Tyr Phe His His Asn
            35                  40                  45

Ser Asp Phe Tyr Ile Pro Lys Ala Thr Leu Lys Asp Ser Gly Ser Tyr
50                  55                  60

Phe Cys Arg Gly Leu Val Gly Ser Lys Asn Val Ser Ser Glu Thr Val
65                  70                  75                  80

Asn Ile Thr Ile Thr Gln Gly Leu Ala Val Ser Thr Ile Ser Ser Phe
                85                  90                  95

Phe Pro Pro Gly Tyr Gln Gly Leu Asn Asp Ile Phe Glu Ala Gln Lys
            100                 105                 110

Ile Glu Trp His Glu Leu Glu Asp Lys Thr His Thr Cys Pro Pro Cys
            115                 120                 125

Pro Ala Pro Glu Ala Ala Gly Gly Pro Ser Val Phe Leu Phe Pro Pro
            130                 135                 140

Lys Pro Lys Asp Thr Leu Met Ile Ser Arg Thr Pro Glu Val Thr Cys
145                 150                 155                 160
```

-continued

```
Val Val Val Asp Val Ser His Glu Asp Pro Glu Val Lys Phe Asn Trp
            165             170             175
Tyr Val Asp Gly Val Glu Val His Asn Ala Lys Thr Lys Pro Arg Glu
            180             185             190
Glu Gln Tyr Asn Ser Thr Tyr Arg Val Val Ser Val Leu Thr Val Leu
    195                 200                 205
His Gln Asp Trp Leu Asn Gly Lys Glu Tyr Lys Cys Lys Val Ser Asn
    210                 215                 220
Lys Ala Leu Gly Ala Pro Ile Glu Lys Thr Ile Ser Lys Ala Lys Gly
225                 230                 235                 240
Gln Pro Arg Glu Pro Gln Val Tyr Thr Leu Pro Pro Ser Arg Asp Glu
            245                 250                 255
Leu Thr Lys Asn Gln Val Ser Leu Thr Cys Leu Val Lys Gly Phe Tyr
            260                 265                 270
Pro Ser Asp Ile Ala Val Glu Trp Glu Ser Asn Gly Gln Pro Glu Asn
            275                 280                 285
Asn Tyr Lys Thr Thr Pro Pro Val Leu Asp Ser Asp Gly Ser Phe Phe
    290                 295                 300
Leu Tyr Ser Lys Leu Thr Val Asp Lys Ser Arg Trp Gln Gln Gly Asn
305                 310                 315                 320
Val Phe Ser Cys Ser Val Met His Glu Ala Leu His Asn His Tyr Thr
            325                 330                 335
Gln Lys Ser Leu Ser Leu Ser Pro Gly Lys
            340                 345
```